(12) United States Patent
Zlokovic et al.

(10) Patent No.: US 7,608,586 B2
(45) Date of Patent: Oct. 27, 2009

(54) SOLUBLE LOW-DENSITY LIPOPROTEIN RECEPTOR RELATED PROTEIN BINDS DIRECTLY TO ALZHEIMER'S AMYLOID-BETA PEPTIDE

(75) Inventors: Berislav V. Zlokovic, Rochester, NY (US); Rashid Deane, Rochester, NY (US)

(73) Assignees: The University of Rochester, New York, NY (US); Socratech L.L.C., Los Angeles, CA (US)

( * ) Notice: Subject to any disclaimer, the term of this patent is extended or adjusted under 35 U.S.C. 154(b) by 0 days.

(21) Appl. No.: 10/558,984

(22) PCT Filed: Jun. 14, 2004

(86) PCT No.: PCT/US2004/019034

§ 371 (c)(1), (2), (4) Date: Dec. 2, 2005

(87) PCT Pub. No.: WO2005/122712

PCT Pub. Date: Dec. 29, 2005

(65) Prior Publication Data

US 2007/0054318 A1 Mar. 8, 2007

Related U.S. Application Data

(60) Provisional application No. 60/477,404, filed on Jun. 11, 2003.

(51) Int. Cl.
*A61K 38/02* (2006.01)
(52) U.S. Cl. ........................................................ 514/12
(58) Field of Classification Search ........................ None
See application file for complete search history.

(56) References Cited

U.S. PATENT DOCUMENTS

| | | | |
|---|---|---|---|
| 4,758,583 A | 7/1988 | Cerami et al. | |
| 4,900,747 A | 2/1990 | Vlassara et al. | |
| 5,202,424 A | 4/1993 | Vlassara et al. | |
| 5,208,154 A * | 5/1993 | Weaver et al. | 435/176 |
| 5,221,628 A * | 6/1993 | Anderson et al. | 436/507 |
| 5,316,754 A | 5/1994 | Vlassara et al. | |
| 5,766,856 A | 6/1998 | Imani et al. | |
| 5,864,018 A | 1/1999 | Morser et al. | |
| 5,932,580 A * | 8/1999 | Levitzki et al. | 514/249 |
| 5,962,245 A | 10/1999 | Li et al. | |
| 6,156,311 A | 12/2000 | Strickland et al. | |
| 6,242,416 B1 * | 6/2001 | Gilchrest et al. | 514/2 |
| 6,410,598 B1 | 6/2002 | Vitek et al. | |
| 6,413,512 B1 | 7/2002 | Houston et al. | |
| 6,428,967 B1 | 8/2002 | Herz et al. | |
| 6,447,775 B1 | 9/2002 | Strickland et al. | |
| 6,472,140 B1 | 10/2002 | Tanzi et al. | |
| 6,677,299 B2 | 1/2004 | Stern et al. | |
| 6,825,164 B1 | 11/2004 | Stern et al. | |
| 7,056,688 B2 | 6/2006 | Herz et al. | |
| 7,192,714 B2 | 3/2007 | Herz et al. | |
| 2002/0172676 A1 * | 11/2002 | Jackowski et al. | 424/140.1 |
| 2004/0038338 A1 | 2/2004 | Koo et al. | |
| 2004/0259159 A1 | 12/2004 | Zlokovic | |
| 2005/0227941 A1 | 10/2005 | Duff et al. | |
| 2005/0239062 A1 | 10/2005 | Zlokovic | |
| 2006/0034848 A1 | 2/2006 | Kinoshita et al. | |
| 2006/0088528 A1 | 4/2006 | Hyman et al. | |
| 2007/0253950 A1 | 11/2007 | Jacobsen | |

FOREIGN PATENT DOCUMENTS

| | | |
|---|---|---|
| WO | WO 97/04794 | 2/1997 |
| WO | WO 01/90758 | 11/2001 |
| WO | WO 02/14519 | 2/2002 |
| WO | WO 2005/122712 | 12/2005 |
| WO | 2007/059242 | 5/2007 |
| WO | 2007/089616 | 8/2007 |

OTHER PUBLICATIONS

Neels et al. 1999. Journal of Biological Chemistry 274:31305-31311.*
Lo et al. 1998. Protein Engineering 11:495-500.*
Bell et al. "Transport pathways for clearance of human Alzheimer's amyloid β-peptide and apolipoproteins E and J in the mouse central nervous system" J. Cereb. Blood Flow & Metab. 27:909-918 (May 2007) but the submitted copy is the earlier available epublication on Nov. 1, 2006.
Bu et al. "39 kDA receptor-associated protein is an ER resident protein and molecular chaperone for LDL receptor-related protein" EMBO J. 14:2269-2280 (1995).
Bu et al. "Receptor-associated protein is a folding chaperone for low density lipoprotein receptor-related protein" J. Biol. Chem. 271:2218-2224 (1996).
Cam et al. "Rapid endocytosis of the low density lipoprotein receptor-related protein modulates cell surface distribution and processing of the β-amyloid precursor protein" J. Biol. Chem. 280:15464-15470 (Apr. 2005).
Deane et al. "LRP/amyloid β-peptide interactionmediates differential brain efflux of Aβ isoforms" Neuron 43:333-344 (Aug. 2004).
Deane et al. "IgG-Assisted age-dependent clearance of Alzheimer's amyloid β peptide by the blood-brain barrier neonatal Fc receptor" J. Neurosci. 25:11495-11503 (Dec. 2005).
Horn et al. "Molecular analysis of ligand binding to the second cluster of complement-type repeats of the low density lipoprotein receptor-related protein" J. Biol. Chem. 272:13608-13613 (1997).

(Continued)

*Primary Examiner*—Daniel E. Kolker
(74) *Attorney, Agent, or Firm*—Nixon & Vanderhye P.C.

(57) ABSTRACT

A soluble derivative of low-density lipoprotein receptor related protein-1 (sLRP-1) binds directly to Alzheimer's amyloid-β peptide (Aβ). This binding may be used to detect Aβ or to separate Aβ from the rest of a subject's body. In Alzheimer's disease, it may be used to provide diagnostic results by detecting Aβ, treatment by removing Aβ, or both.

40 Claims, 7 Drawing Sheets

OTHER PUBLICATIONS

Figures 1A, 1B, 1C:
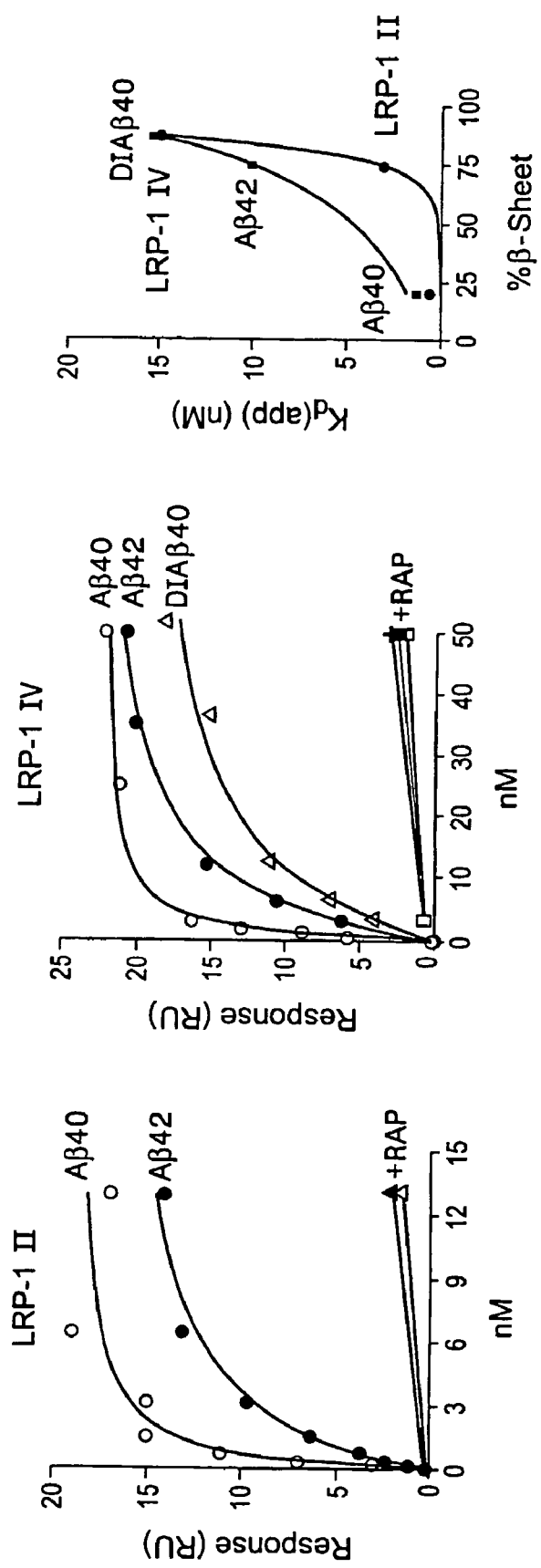

Moestrup et al. "α₂-Macroglobulin-proteinase complexes, plasminogen activator inhibitor type-1-plasminogen activator complexes, and receptor-associated protein bind to a region of the α₂-macroglobulin receptor containing a cluster of eight complement-type repeats" J. Biol. Chem. 268:13691-13696 (1993).

Sagare et al. "Clearance of amyloid-β by circulating lipoprotein receptors" Nature Med. doi:10.1038/nm1635, 21 pages, the submitted copy is the earlier available epublication on Aug. 12, 2007.

Willnow et al. "Molecular dissection of ligand binding sites on the low density lipoprotein receptor-related protein" J. Biol. Chem. 269:15827-15832 (1994).

Deane et al. "RAGE mediates amyloid-β peptide transport across the blood-brain barrier and accumulation in brain" Nature Medicine 9:907-913 (2003).

DeMattos et al. "Peripheral anti-Aβ antibody alters CNS and plasma Aβ clearance and decreases brain Aβ burden in a mouse model of Alzheimer's disease" Proc. Natl. Acad. Sci. USA 98:8850-8855 (2001).

Ghersi-Egea et al. "Fate of cerebrospinal fluid-borne amyloid β-peptide: Rapid clearance into blood and appreciable accumulation by cerebral arteries" J. Neurochem. 67:880-883 (1996).

Ghilardi et al. "Intra-arterial infusion of [$^{125}$I]Aβ1-40 labels amyloid deposits in the aged primate brain in vivo" NeuroReport 7:2607-2611 (1996).

Jordan et al. "Isoform-specific effect of apolipoprotein E on cell survival and beta-amyloid-induced toxicity in rat hippocampal pyramidal neuronal cultures" J. Neurosci. 18:195-204 (1998).

Iwata et al. "Identification of the major Aβ$_{1-42}$-degrading catabolic pathway in brain parenchyma: Suppression leads to biochemical pathological deposition" Nature Medicine 6:143-150 (2000).

Lucarelli et al. "Expression of receptors for native and chemically modified low-density lipoproteins in brain microvessels" FEBS Letters 401:53-58 (1997).

Mackic et al. "Human blood-brain barrier receptors for Alzheimer's amyloid-β 1-40. Asymmetrical binding, endocytosis, and transcytosis at the apical side of brain microvascular endothelial cell monolayer" J. Clin. Invest. 102:734-743 (1998).

Mackic et al. "Cerebrovascular accumulation and increased blood-brain barrier permeability to circulating Alzheimer's amyloid β peptide in aged squirrel monkey with cerebral amyloid aniopathy" J. Neurochem. 70:210-215 (1998).

Maness et al. "Passage of human amyloid β-protein 1-40 across the murine blood-brain barrier" Life Sciences 55:1643-1650 (1994).

Martel et al. "Isoform-specific effects of apolipoprioteins E2, E3, and E4 on cerebral capillary sequestration and blood-brain barrier transport of circulating Alzheimer's amyloid β" J. Neurochem. 69:1995-2004 (1997).

Mattson et al. "Amyloid ox-tox transducers" Nature 382:674-675 (1996).

Narita et al. "α2-macroglobulin complexes with and mediates the endocytosis of β-amyloid peptide via cell surface low-density lipoprotein receptor-related protein" J. Neurochem. 69:1904-1911 (1997).

Poduslo et al. "Permeability and residual plasma volume of human, Dutch variant, and rat amyloid β-protein 1-40 at the blood-brain barrier" Neurobiol. Dis. 4:27-34 (1997).

Qiu et al. "α2-macroglobulin enhances the clearance of endogenous soluble β-amyloid peptide via low-density lipoprotein receptor-related protein in cortical neurons" J. Neurochem. 73:1393-1398 (1999).

Schmidt et al. "Receptor for advanced glycation end products (AGEs) has a central role in vessel wall interactions and gene activation in response to circulating AGE proteins" Proc. Natl. Acad. Sci. USA 91:8807-8811 (1994).

Shibata et al. "Clearance of Alzheimer's amyloid-β 1-40 peptide from brain by LDL receptor-related protein-1 at the blood-brain barrier" J. Clin. Invest. 106:1489-1499, 2000.

Yan et al. "RAGE and amyloid-β peptide neurotoxicity in Alzheimer's disease" Nature 382:685-691 (1996).

Yan et al. "Receptor-dependent cells stress and amyloid accumulation in systemic amyloidosis" Nature Medicine 6:643-651 (2000).

Zlokovic "Can blood-brain barrier play a role in the development of cerebral amyloidosis and Alzheimer's disease pathology" Neurobiol. Dis. 4:23-26 (1997).

Zlokovic et al. "Glycoprotein 330/megalin: Probable role in receptor-mediated transport of apolipoprotein J alone and in a complex with Alzheimer disease amyloid β at the blood-brain and blood-cerebrospinal fluid barriers" Proc. Natl. Acad. Sci. USA 93:4229-4234 (1996).

Zlokovic et al. "Clearance of amyloid β-peptide from brain: Transport or metabolism?" Nature Medicine 6:718-719 (2000).

Zlokovic et al. "Role of low-density lipoprotein receptor related protein-1 in vascular clearance of amyloid β 1-40 peptide from brain" Society for Neuroscience Abstracts 26:275.18 (2000).

Deane et al. "RAGE (Yin) versus LRP (Yang) balance regulates Alzheimer amyloid β-peptide clearance through transport across the blood-brain barrier" Stroke 35:2628-2631 (2004).

DeMattos et al. "Brain to plasma amyloid-β efflux: A measure of brain amyloid burden in a mouse model of Alzheimer's disease" Science 295:2264-2267 (2002).

Hardy et al. "The amyloid hypothesis of Alzheimer's disease: Progress and problems on the road to therapeutics" Science 297:353-356 (2002).

Herz et al. "LRP: A multifunctional scavenger and signaling receptor" J. Clin. Invest. 108:779-784 (2001).

Hsiao et al. "Correlative memory deficits, Aβ elevation, and amyloid plaques in transgenic mice" Science 274:99-103 (1996).

Hyman et al. "Role of the low-density lipoprotein receptor-related protein in β-amyloid metabolism and Alzheimer disease" Arch. Neurol. 57:pp. 646 and 650 only (2000).

Kang et al. "Genetic association of the low-density lipoprotein receptor-related protein gene (LRP), and apolipoprotein E receptor, with late-onset Alzheimer's disease" Neurology 49:56-61 (1997).

Kang et al. "Modulation of amyloid β-protein clearance and Alzheimer's disease susceptibility by the LDL receptor-related protein pathway" J. Clin. Invest. 106:1159-1166 (2000).

Kounnas et al. "LDL receptor-related protein, a multifunctional ApoE receptor, binds secreted β-amyloid precursor protein and mediates its degradation" Cell 82:331-340 (1995).

Lorenzo et al. "Amyloid β interacts with the amyloid precursor protein: A potential toxic mechanism in Alzheimer's disease" Nat. Neurosci. 3:460-464 (2000).

Melman et al. "Proteasome regulates the delivery of LDL receptor-related protein into the degradation pathway" Mol. Biol. Cell 13:3325-3335 (2002).

Pietrzik et al. "The cytoplasmic domain of the LDL receptor-related protein regulates multiple steps in APP processing" EMBO J. 21:5691-5700 (2002).

Takahashi et al. "Intraneuronal Alzheimer Aβ42 accumulates in multivesicular bodies and is associated with synaptic pathology" Am. J. Pathol. 161:1869-1879 (2002).

Ulery et al. "Modulation of β-amyloid precursor protein processing by the low density lipoprotein receptor-related protein (LRP)" J. Biol. Chem. 275:7410-7415 (2000).

Ulery et al. "LRP in Alzheimer's disease: Friend or foe?" J. Clin. Invest. 106:1077-1079 (2000).

Van Uden et al. "LDL receptor-related protein (LRP) in Alzheimer's disease: Towards a unified theory of pathogenesis" Microsc. Res. Tech. 15:268-272 (2000) (abstract).

Van Uden et al. "Increased extracellular amyloid deposition and neurodegeneration in human amyloid precursor protein transgenic mice deficient in receptor-associated protein" J. Neurosci. 22:9298-9304 (2002).

Vinters et al. "Amyloidosis of cerebral arteries" Adv. Neurol. 92:105-112 (2003).

Willnow et al. "Functional expression of low density lipoprotein receptor-related protein is controlled by receptor-associated protein in vivo" Proc. Natl. Acad. Sci. USA 92:4537-4541 (1995).

Willnow et al. "RAP, a specialized chaperone, prevents ligand-induced ER retention and degradation of LDL receptor-related endocytic receptors" EMBO J. 15:2632-2639 (1996).

Wolozin et al. "A fluid connection: Cholesterol and Aβ" Proc. Natl. Acad. Sci. USA 98:5371-5373 (2001).

Zerbinatti et al. "Increased soluble amyloid-β peptide and memory deficits in amyloid model mice overexpressing the low-density lipoprotein receptor-related protein" Proc. Natl. Acad. Sci. USA 101:1075-1080 (2004).

Deane et al. "apoE isoform-specific disruption of amyloid beta peptide clearance from mouse brain" J. Clin. Invest. 118:4002-4013 (2008).

Kinoshita et al. "Demonstration of fluorescence resonance energy transfer of two sites of interaction between the low-density lipoprotein receptor-related protein and the amyloid precursor protein: Role of the intracellular adapter protein Fe65" J. Neurosci. 21:8354-8361 (2001).

Knauer et al. "Cell surface APP751 forms complexes with protease nexin 2 ligands and is internalized via the low density lipoprotein receptor-related protein (LRP)" Brain Res. 740:6-14 (1996).

Moir et al. "Relative increase in Alzheimer's disease of soluble forms of cerebral Aβ amyloid protein precursor containing the Kunitz protease inhibitory domain" J. Biol. Chem. 273:5013-5019 (1998).

Moir et al. "LRP-mediated clearance of Aβ is inhibited by KPI-containing isoforms of APP" Curr. Alzheimer Res. 2:269-273 (2005).

Olsson et al. "Measurement of α- and β-secretase cleaved amyloid precursor protein in cerebrospinal fulid from Alzheimer patients" Exp. Neurol. 183:74-80 (2003).

Pietrzik et al. "FE65 constitutes the functional link between the low-density lipoprotein receptor-related protein and the amyloid precursor protein" J. Neurosci. 24:4259-4265 (2004).

Rebeck et al. "Multiple, diverse senile plaque-associated proteins are ligands of an apolipoprotein E receptor, the $\alpha_2$-macroglobulin receptor/low-density-lipoprotein receptor-related protein" Ann. Neurol. 37:211-217 (1995).

Rebeck et al. "Association of membrane-bound amyloid precursor protein APP with the apolipoprotein E receptor LRP" Mol. Brain Res. 87:238-245 (2001).

Sagare et al. Clearance of amyloid-β by circulating lipoprotein receptors Nature Med. 13:1029-1031 and supplementary information (2007).

Selkoe "Alzheimer's disease: Genes, proteins, and therapy" Physiol. Rev. 81:741-766 (2001).

Sisodia et al. "Identification and transport of full-length amyloid precursor proteins in rat peripheral nervous system" J. Neurosci. 13:3136-3142 (1993).

Smith et al. "Platelet coagulation factor XIa-inhibitor, a form of Alzheimer amyloid precursor protein" Science 248:1126-1128 (1990).

Tanzi et al. "Clearance of Alzheimer's Aβ peptide: The many roads to perdition" Neuron 43:605-608 (2004).

Urmoneit et al. "Cerebrovascular smooth muscle cells internalize Alzheimer amyloid beta protein via a lipoprotein pathway: Implications for cerebral amyloid angiopathy" Lab. Invest. 77:157-166 (1997).

Waldron et al. "LRP1 modulates APP trafficking along early compartments of the secretory pathway" Neurobiol. Dis. 31:188-197 (2008).

Ye et al. "Apolipoprotein (apo) E4 enhances amyloid β peptide production in cultured neuronal cells: ApoE structure as a potential therapeutic target" Proc. Natl. Acad. Sci. USA 102:18700-18705 (2005).

Yoon et al. "Low-density lipoprotein receptor-related protein promotes amyloid precursor protein trafficking to lipid rafts in the endocytic pathway" FASEB J. 21:2742-2752 (2007).

Quinn et al. "Soluble low density lipoprotein-related protein (LRP) circulates in human plasma" J. Biol. Chem. 272:23946-23951 (Jan. 2002).

Westein et al. "The α-chains of C4b-binding protein mediate complex formation with low density lipoprotein receptor-related protein" J. Biol. Chem. 277:2511-2516 (Sep. 1997).

Supplementary European Search Report, five pages (May 2009).

* cited by examiner

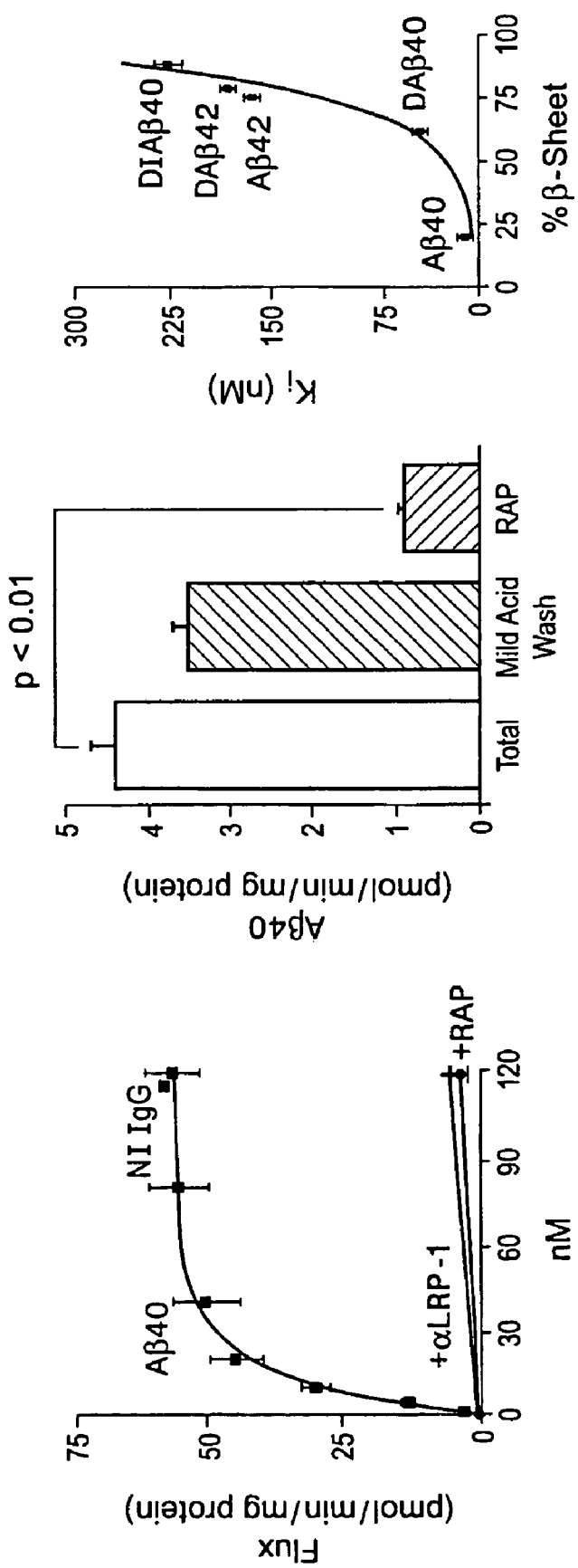

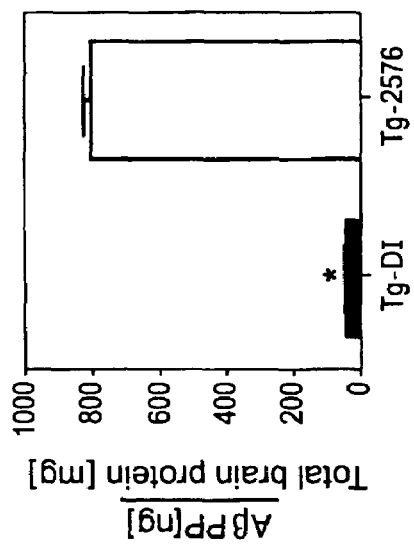
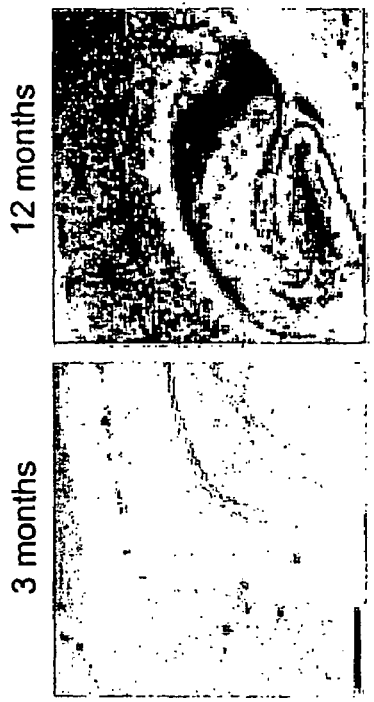
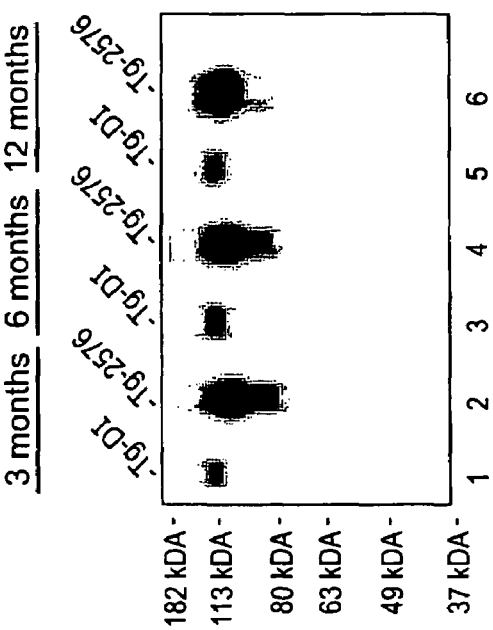
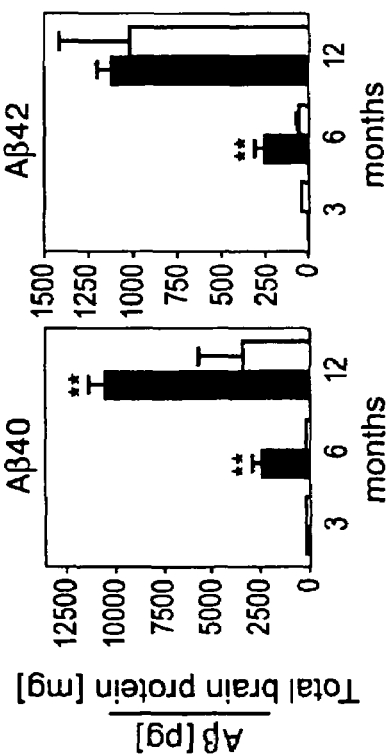
Fig. 5A
Fig. 5B
Fig. 5C
Fig. 5D

SOLUBLE LOW-DENSITY LIPOPROTEIN RECEPTOR RELATED PROTEIN BINDS DIRECTLY TO ALZHEIMER'S AMYLOID-BETA PEPTIDE

CROSS-REFERENCE TO RELATED APPLICATIONS

This application is a national phase application under 35 U.S.C 371 Int'l Patent Appln. No. PCT/US2000/019034, filed Jun. 14, 2004; which claims the benefit of provisional Appln. No. 60/477,404, filed Jun. 11, 2003 the entire contents of which are hereby incorporated by reference.

STATEMENT REGARDING FEDERALLY-SPONSORED RESEARCH

The U.S. government has certain rights in this invention as provided for by the terms of grants AG16223 and NS34467 awarded by the National Institutes of Health.

FIELD OF THE INVENTION

The invention relates to a soluble derivative of low-density lipoprotein receptor related protein-1 (sLRP-1) and its direct binding to Alzheimer's amyloid-β peptide (Aβ). This binding may be used to detect Aβ or to separate Aβ from the rest of a subject's body. In Alzheimer's disease, the invention may be used to provide diagnostic results by detecting Aβ, treatment by removing Aβ, or both.

BACKGROUND OF THE INVENTION

Amyloid-β peptide (Aβ) is central to the pathology of Alzheimer's disease; it is the main constituent of brain parenchymal and vascular amyloid. Aβ extracted from senile plaques contains mainly $A\beta_{1-140}$ and $A\beta_{1-42}$, while vascular amyloid is mainly $A\beta_{1-39}$ and $A\beta_{1-40}$. The major soluble form of Aβ which is present in the blood, cerebrospinal fluid (CSF), and brain is $A\beta_{1-40}$. Soluble Aβ which is circulating in the blood, CSF, and brain interstitial fluid (ISF) may exist as free peptide and/or associated with different transport binding proteins such as apolipoprotein E (apoE), apolipoprotein J (apoJ), transthyretin, other lipoproteins, albumin, and alpha2-macroglobulin ($\alpha_2$M).

LRP-1 binds amyloid β-peptide (Aβ) precursor protein (APP), apolipo-protein E (apoE) and $\alpha_2$-macroglobulin ($\alpha_2$M), (Herz and Strickland, 2001). But the exact biochemical mechanism(s) by which LRP-1 contributes to the onset of neurotoxic Aβ accumulations is unclear. LRP-1 binds secreted APP and influences its degradation (Kounnas et al., 1995) and processing (Pietrzik et al., 2002) leading to increased Aβ production (Ulery et al., 2000). It also mediates endocytosis of $\alpha_2$M-Aβ complexes in fibroblasts (Narita et al., 1997; Kang et al., 2000) and of apoE-Aβ and $\alpha_2$M-Aβ complexes in neurons in vitro (Jordan et al., 1998; Qiu et al., 1999). Overexpression of functional LRP-1 minireceptors in neurons of Alzheimer's PDAPP mice results in an age-dependent increase of soluble Aβ in the brain (Zerbinatti et al., 2004), which suggests that LRP-1 on neurons in vivo does not mediate Aβ clearance from brain.

Peripheral Aβ binding agents, e.g., an anti-Aβ antibody (DeMattos et al., 2002a), a soluble form of the receptor for advanced glycation endproducts, sRAGE (Deane et al., 2003) and/or ganglioside M1 and gelsolin (Matsuoka et al., 2003), rapidly clear Aβ from brain in vivo in various transgenic APP over-expressing mice. The idea that LRP-1 along the brain capillary membranes is a major clearance mechanism for Aβ in vivo has been. supported by findings demonstrating that intracerebrally infused $A\beta_{1-40}$ undergoes rapid LRP-1-mediated transcytosis across the blood-brain barrier (BBB) (Shibata et al., 2000). Several questions, however, regarding a possible role of LRP-1 (including $A\beta_{1-40}$, $A\beta_{1-42}$, and mutant versions thereof) as a cargo/clearance receptor for brain Aβ remained unanswered. Whether Aβ is a direct ligand for LRP-1 initiating its own efflux from brain through interaction with the receptor at the BBB is not known. Reduced levels of LRP-1 in the brain were found in AD (Kang et al., 1997; Kang et al., 2000; Shibata et al., 2000). Whether high extracellular Aβ accumulations affect LRP-1 expression at the Aβ clearance site(s) in the brain is riot known.

But it was not previously demonstrated that low-density lipoprotein receptor related protein-1 (LRP-1) binds directly to Aβ. Cell surface receptors such as the receptor for advanced glycation end products (RAGE), scavenger type A receptor (SR-A), LRP-1, and low-density lipoprotein receptor related protein-2 (LRP-2) bind Aβ at low nanomolar concentrations as free peptide (e.g., RAGE, SR-A), and/or in complex with apoE, apoJ, or $\alpha_2$M (e.g., LRP-1, LRP-2). But it was not previously demonstrated that a soluble derivative of LRP-1 is able to directly bind Aβ in a bimolecular interaction.

WO 01/90758 and U.S. patent application Ser. No. 10/296, 168 describe LRP-1's role in mediating vascular clearance of Aβ from the brain. It was taught that increasing LRP-1 expression or its activity can be used to remove Aβ and thereby treat an individual with Alzheimer's disease or at risk for developing the disease. A direct interaction between LRP-1 and Aβ was not described, nor was it taught or suggested that the two molecules are able to bind in solution without another ligand of LRP-1 such as apoE, apoJ, $\alpha_2$M, transthyretin, other lipoproteins, albumin, or RAP.

Here, it is demonstrated that LRP-1 and Aβ directly interact with each other (i.e., the two molecules are sufficient by themselves to specifically interact with each other) and this interaction on brain capillary membranes regulates retention of high B-sheet content neurotoxic $A\beta_{1-42}$ and vasculotropic mutant Aβ while clearing $A\beta_{1-40}$. LRP-1 mediates differential efflux of amyloid β-peptide isoforms from brain. $A\beta_{1-40}$ binds to an immobilized LRP-1 fragment containing clusters II and IV with high affinity (Kd=0.6 nM to 1.2 nM) compared to $A\beta_{1-42}$ and mutant Aβ. LRP-mediated Aβ clearance and transport across the blood-brain barrier in mice are substantially reduced by high B-sheet content in Aβ and deletion of the receptor-associated protein gene. Despite low Aβ production in the brain, transgenic mice expressing low LRP-1-clearance mutant Aβdevelop robust Aβ accumulations in the brain earlier than Tg-2576 Aβ-over-producing mice. At pathological concentrations (>1 μM), Aβ promotes LRP-1 degradation in brain endothelium consistent with reduced LRP-1 brain capillary levels observed in Aβ-accumulating transgenic mice, AD and patients with cerebrovascular β-amyloidosis. Thus, low affinity LRP-1/Aβ interaction and/ or loss of LRP-1 at the BBB mediate brain accumulation of neurotoxic Aβ.

Receptor-associated proteins and receptor-mediated cell signaling are not required. Deletion of the RAP gene (Van Uden et al., 2002) which is associated with greatly reduced LRP-1 expression in the brain and at the BBB, but not deletion of the genes for the VLDL receptor or the LDL receptor, almost completely precluded rapid efflux of A from brain. Consistent with the findings here, LRP-1 levels were substantially reduced in brain microvessels in situ in a transgenic Aβ-accumulating animal model and patients with AD and cerebro-vascular β-amyloidosis.

New and nonobvious pharmaceutical and diagnostic compositions, and methods of treatment and diagnosis are taught herein to be applicable to the formation of amyloid and its role in disease. Other advantages of the invention are discussed below or would be apparent to a person skilled in the art from that discussion.

SUMMARY OF THE INVENTION

A soluble derivative of low-density lipoprotein receptor related protein-1 (sLRP-1) is provided in one embodiment of the invention. The soluble LRP-1 derivative may be comprised of one or more domains derived from LRP-1 and, optionally, one or more domains not derived from LRP-1 (i.e., heterologous domains which do not exist in the native protein). It is preferred that at least the cluster II and/or cluster IV domain(s) is contained therein; it may consist essentially of only cluster II and/or cluster IV domain(s). The soluble LRP-1 derivative may or may not contain other optional domains: a signal domain which directs secretion out of the cell (e.g., a hydrophobic signal sequence which targets nascent polypeptide to endoplasmic reticulum, translocates polypeptide across the membrane, and transports polypeptide with any modifications through the secretory pathway) and a domain which attaches a polypeptide to a lipid bilayer (e.g., a transmembrane domain for docking across or a lipid domain for insertion into the membrane). The soluble LRP-1 derivative may be reversibly or irreversibly attached to a solid substrate (e.g., using a covalent bond which is chemically labile or stable, respectively). It is not identical to native LRP-1 so one or more domains of the native amino acid sequence must be mutated (e.g., substitution, addition, deletion) to make the LRP-1 soluble and to retain its ability to bind Aβ. It is also preferred that human or another mammal be used as the source, and an undetectable immune response be elicited in the subject in whom the soluble LRP-1 derivative is administered (e.g., derived from human or a humanized mammalian LRP-1 derivative infused into a human subject).

The soluble LRP-1 derivative may be used in treatment as a medicament (e.g., therapy in a subject having the disease or prophylaxis in a subject at risk for developing the disease) or diagnosis as an agent for detection of Aβ. A therapeutic or prophylactic composition is comprised of soluble LRP-1 derivative and at least one pharmaceutically-acceptable carrier (e.g., a solution of physiological salt and buffer). It may inactivate Aβ by removing Aβ from the subject through the body's circulatory systems or by machine, or by reducing deposition of amyloid. A diagnostic composition is comprised of soluble LRP-1 derivative and at least one detectable label (e.g., a moiety for chromatic, enzymatic, fluorescent, luminescent, magnetic or paramagnetic, or radioactive detection). The soluble LRP-1 derivative and the detectable label may or may not be covalently attached. Alternatively, they may be attached though one or more specific binding pairs. Binding may occur inside or outside the subject's body, in solution or with one of them immobilized on a substrate. Soluble LRP-1 derivative bound to Aβ may be detected in a specimen prepared from a body fluid or tissue using laboratory assay (i.e., in vitro diagnostics) or in the body by fluoroscopic, magnetic resonance, or radiographic imaging (i.e., in vivo diagnostics).

Further aspects of the invention will be apparent to a person skilled in the art from the following detailed description and claims, and generalizations thereto.

BRIEF DESCRIPTIONS OF THE DRAWINGS

FIG. 1 shows surface plasmon resonance (SPR) analysis of the interaction between Aβ and recombinant LRP-1 fragments. FIG. 1A: $A\beta_{1-40}$ (Aβ40) and $A\beta_{1-42}$ (Aβ42) binds to LRP-1 cluster II (LRP-1 II) which is immobilized on a CM5 chip at a density of 10 fmol/mm$^2$ under the conditions described below. Incubation conditions as described under Materials and Methods. FIG. 1B: Peptide $A\beta_{1-40}$ (Aβ40), $A\beta_{1-42}$ (Aβ42), or Dutch/Iowa mutant $A\beta_{1-40}$ (DIAβ40) binds to immobilized LRP-1 cluster IV (LRP-1 IV) under the same conditions. FIG. 1C: Kinetic parameters for the binding of different Aβ species to LRP-1 were plotted against the content of β-sheets in Aβ peptides as determined by circular dichroism analysis. Apparent affinity constants $K_{d(app)}$ were deduced from the ratios of $k_{off(app)}/k_{on(app)}$ as described under Materials and Methods. Mean±SEM (n=3-5); SEM≦5% of the mean in FIGS. 1A-1B. $K_{d(app)}$ (mean±SD) values were determined from 6 to 9 different concentrations of Aβ and 3 to 5 independent measurements at each concentration. RAP, receptor-associated protein (500 nM); RU, resonance units.

FIG. 2 shows LRP-1-mediated in vitro clearance of Aβ by mouse brain capillaries. FIG. 2A: Rapid saturable $A\beta_{1-40}$ uptake on isolated brain capillaries was determined with $^{125}$I-$A\beta_{1-40}$ as a ligand (1 nM) in the presence of increasing concentrations of unlabeled Aβ (1 nM to 120 nM) at 37° C. within 1 min. $A\beta_{1-40}$ brain capillary uptake at 120 nM was completely inhibited by RAP (1 μM) or anti-LRP-1-specific N20 polyclonal antibody (αLRP-1, 60 μg/ml), but not by a non-immune IgG (NI IgG, 60 μg/ml). FIG. 2B: $^{125}$I-$A\beta_{1-40}$ uptake at 37° C. on isolated brain capillaries before (total) and after treatment with a cold stop/strip 0.2 M acetic acid solution (mild acid wash) was blocked by RAP (500 nM). FIG. 2C: Inhibitory constants $K_i$ for LRP-mediated brain capillary clearance of Aβ peptides were determined using $^{125}$I-$A\beta_{1-40}$ (2 nM) as a ligand and unlabeled peptide $A\beta_{1-40}$ (Aβ40), $A\beta_{1-42}$ (Aβ42), Dutch mutant $A\beta_{1-40}$ (DAβ40), Dutch mutant $A\beta_{1-42}$ (DAβ42), or Dutch/Iowa mutant $A\beta_{1-40}$ (DIAβ40) at an inhibitory concentration of 40 nM. Ki values are plotted against β-sheet content in Aβ determined by circular dichroism. Mean±SEM (n=3-5).

FIG. 3 shows low LRP-1-mediated Aβ clearance by brain microvessels in RAP-null mice. FIG. 3A: LRP-1 levels in brain capillaries isolated from wild-type and RAP-null (RAP−/−) mice was determined by Western blot analysis using anti-LRP-1 β-chain specific IgG (5A6, LRP-85). Scanning densitometry of the intensity of LRP-1 bands relative to β-actin in wild-type (control, open bar) and RAP−/− (closed bar) mice. FIG. 3B: LRP-1 and CD31 (endothelial cell marker) were localized in brain tissue sections (scale bar=50 μm) in wild-type (control) and RAP-null mice using double immunostaining. FIG. 3C: LRP-1-positive vascular expression profiles in different brain regions were determined in wild-type mice (open bars) and RAP-null mice (closed bars). FIG. 3D: Reduced brain capillary in vitro clearance of $^{125}$I-labeled peptide $A\beta_{1-40}$ (Aβ40), $A\beta_{1-42}$ (Aβ42), or Dutch/Iowa mutant $A\beta_{1-40}$ (DIAβ40); in wild-type mice (open bars) and RAP-null mice (closed bars) was studied at 1 nM peptide concentration. *P<0.01 RAP-null compared to controls; anti-LRP-1-specific N20 polyclonal antibody (αLRP-1, 60 μg/ml). Mean±SEM (n=3-5).

FIG. 4 shows LRP-1-mediated transport of Aβ across the mouse blood-brain barrier (BBB) in vivo. FIG. 4A: LRP-1- mediated clearance at the BBB of Dutch/Iowa mutant $A\beta_{1-40}$ (DIAβ40, open points) was compared to wild-type $A\beta_{1-40}$ (Aβ40, solid points) determined 30 min after microinjection of radio-iodinated ligands ($^{125}$I-Aβ) in brain ISF at different Aβ carrier concentrations (1 nM to 120 nM). RAP (1 μM), anti-LRP-1-specific N20 polyclonal antibody (αLRP-1, 60 μg/ml), or non-immune IgG (NI IgG, 60 μg/ml; closed square). **P <0.01 and *P<0.05 for $DIA\beta_{1-40}$ vs. $A\beta_{1-40}$. FIG. 4B: Elimination of $^{125}$I-labeled peptide $A\beta_{1-40}$ (Aβ40), $A\beta_{1-42}$ (Aβ42), or Dutch/Iowa mutant $A\beta_{1-40}$ (DIAβ40) from brain ISF via transport across the BBB was studied at a carrier concentration of 40 nM in the absence or presence of unlabeled peptide at an inhibittory concentration of 120 nM. Intact $^{125}$I-labeled Aβ monomers was determined by HPLC analysis of brain homogenates 30 min after microinfusion in brain ISF (insets above the bars). FIG. 4C: Inhibitory constants $K_i$ for LRP-1-mediated efflux from brain via transport across the BBB of peptide $A\beta_{1-40}$ (Aβ40), $A\beta_{1-42}$ (Aβ42), or Dutch/Iowa mutant $A\beta_{1-40}$ (DIAβ40) was determined with $^{125}$I-$A\beta_{1-40}$ at a carrier concentration of 40 nM and unlabeled peptide at an inhibitory concentration of 120 nM. $K_i$ values are plotted against β-sheet content in Aβ determined by circular dichroism. FIG. 4D: Peptide $A\beta_{1-40}$ (Aβ40) or $A\beta_{1-42}$ (Aβ42) does not exhibit rapid efflux across the BBB in RAP null mice (RAP−/−; closed bars) as compared to wild-type mice (control, open bars). Mean±SEM (n=3-8).

Figure 5E:
Figure 5F:
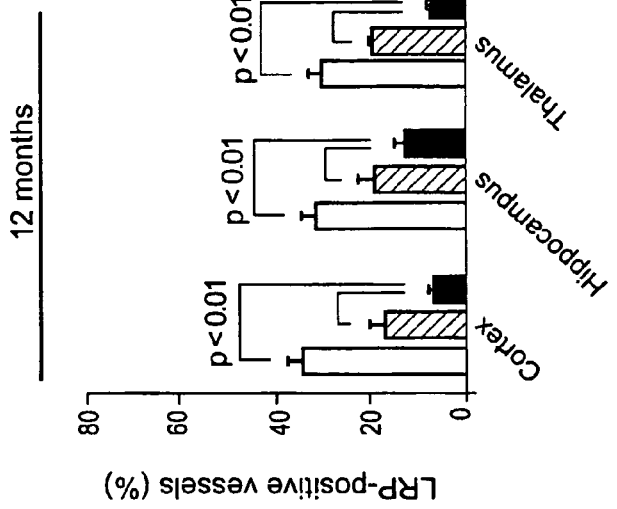
Figure 5G:
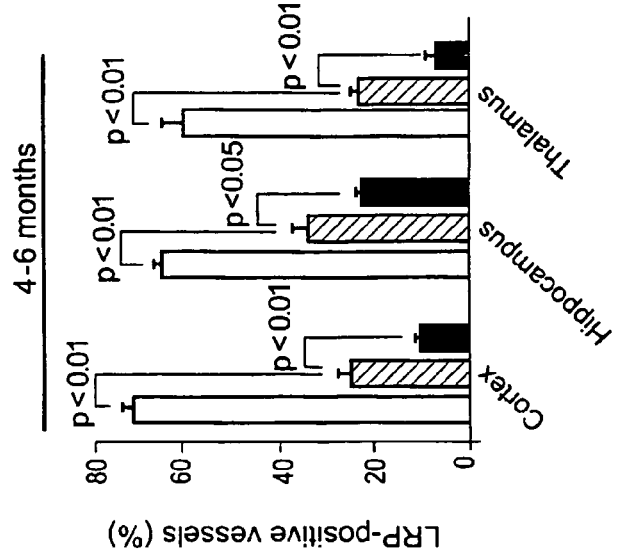

FIG. 5 shows that Aβ accumulated in transgenic mice expressing low LRP-1 -clearance mutant Aβ vs. wild-type Aβ. FIG. 5A: Human APP in the brain of transgenic mice expressing mutant APP harboring both Dutch and Iowa mutations (Tg-DI mice) was compared to Tg-2576 mice using immunoblot analysis. FIG. 5B: APP levels in the brain of Tg-DI mice and Tg-2576 mice at 6 months of age was determined by quantitative immunoblot analysis. FIG. 5C: Brain accumulation of low LRP-1-clearance Dutch/Iowa mutant peptide $A\beta_{1-40}$ or $A\beta_{1-42}$ (Aβ40 and Aβ42, respectively; black bars) in Tg-DI mice was compared to wild-type peptide $A\beta_{1-40}$ or $A\beta_{1-42}$ (Aβ40 and Aβ42, respectively; gray bars) in Tg-2576 mice. FIG. 5D: Early deposits of Dutch/Iowa mutant Aβ in the brain of Tg-DI mice at 3 months of age, and abundant deposits at 12 months of age (bar=200 μm) are shown. FIG. 5E: Intracerebral microvascular Aβ deposits in Tg-DI mice at 12 months of age was detected by immunostaining for Aβ (bar=50 μm). FIG. 5F: LRP-1 -positive brain microvessels in Tg-DI mice (black bars) or Tg-2576 mice (gray bars) were compared to controls (open bars) at 4-6 months of age. FIG. 5G: LRP-1-positive microvessels in Tg-DI mice (black bars), Tg-2576 mice (gray bars) and controls (open bars) are compared at 12 months of age. Mean±SEM (n=4 mice). *P<0.001; **P<0.01 in FIG. 5B-5C for APP and Aβ levels in Tg-DI mice compared to Tg-2576 mice.

DESCRIPTION OF SPECIFIC EMBODIMENTS OF THE INVENTION

Mature low-density lipoprotein receptor related protein-1 (LRP-1) is comprised of five different types of domains: (i) ligand-binding cysteine-rich repeats, (ii) epidermal growth factor (EGF) receptor-like cysteine-rich repeats, (iii) YWTD repeats, (iv) transmembrane domain, and (v) cytoplasmic domain. The signal for entry into the secretory pathway is cleaved after translocation. Ligand-binding-type repeats in LRP-1 occur in clusters containing between two and eleven repeats. Most of the known ligands for LRP-1 that have had their binding sites mapped interact with these ligand-binding-type domains. They are followed by EGF precursor homology domains, which are comprised of two EGF repeats, six YWTD repeats arranged in a propeller-like structure, and another EGF repeat. Six EGF repeats precede the transmembrane domain. The cytoplasmic domain is comprised of two NPxY repeats that serve as docking sites for the endocytosis machinery and for cytoplasmic adaptor and scaffolding proteins which are involved in cell signaling. The heavy chain of LRP-1 (515 kDa) contains four ligand-binding domains (clusters I to IV) and the light chain of LRP-1 (85 kDa) contains the transmembrane and cytoplasmic domains. A soluble LRP-1 derivative may be comprised of only the heavy chain or a fragment thereof.

LRP-1 recognizes at least 30 different ligands which represent several families of proteins, which include lipoproteins, proteinases, proteinase-inhibitor complexes, extracellular matrix (ECM) proteins, bacterial toxins, viruses, and various other intracellular proteins. By far the largest group of ligands that are recognized by LRP-1 are either proteinases or molecules associated with regulating proteolytic activity. Certain serine proteinases and metalloproteinases bind directly to LRP-1, while a number of other proteinases only bind once complexed with their specific inhibitors. These inhibitors are only recognized by LRP-1 following a conformation change that occurs in them after proteolytic cleavage or reaction with small amines. In contrast, LRP-1 recognizes both the native and complexed forms of tissue factor pathway inhibitor (TFPI). LRP-1 also binds to the multimeric matrix proteins thrombospondin-1 and thrornbospondin-2 and delivers *Pseudomonas* exotoxin A and minor-group human rhinovirus into cells. In addition, LRP-1 recognizes a number of intracellular proteins, including HSP96, HIV-1 Tat protein, and RAP, an endoplasmic reticulum resident protein that functions as a molecular chaperone for LRP-1 and other LDL receptor family members.

How does LRP-1 specifically recognize this variety of ligands? Crystallographic and nuclear magnetic resonance studies of individual ligand-binding domains have revealed that amino acid sequence variability in short loops of each ligand-binding domain results in a unique contour surface and charge density for the repeats. LRP-1 "minireceptors" have been made by fusing different ligand-binding domains to the LRP-1 light chain and measuring the ability to mediate the endocytosis of individual ligands following expression in cells. Alternatively, soluble LRP-1 fragments made by recombinant technology and representing the different ligand-binding domains are screened for their ability to bind different ligands in vitro. For example, the short loops responsible for Aβ binding may be grafted onto a heterologous polypeptide (cf. humanization of rodent antibodies to reduce their immunogenicity) to make a soluble LRP-1 derivative which may or may not be attached to a substrate.

A "fragment" is a particular derivative of LRP-1 with a molecular weight less than the molecular weight of full-length LRP-1. The molecular weight of a soluble derivative is preferably between the molecular weight of a single ligand-binding domain and the heavy chain of LRP-1 (515 kDa). For example, soluble LRP-1 derivatives may be from about 35 kDa to about 55 kDa, but both smaller and larger fragment are possible. In particular, derivatives comprising cluster II (i.e., Arg786 to Leu1165 as numbered in Herz et al., 1988) and/or cluster IV (i.e., His3313 to Leu3759 as numbered in Herz et al., 1988) are preferred. The LRP-1 molecule, its amino acid and nucleotide sequence, or its mature form may be derived from human (e.g., accession CAA32112, NP_002323, Q07954 or S02392), other mammals (e.g., cow, guinea pig, mouse, or rat), or polymorphic and mutant variants thereof. Although the full-length LRP-1 might be chemically manipulated (e.g., chemical cleavage or enzymatic proteolysis) to make polypeptide fragments, genetic manipulation of polynucleotides to make those fragments by recombinant technology in a bacterium, mold or yeast, insect, or mammalian cell or organism is preferred. A genetic chimera may be used to fuse soluble LRP-1 derivative to one or more heterologous domains; it may be introduced into cells or organisms (e.g., nuclear transfer, transfection, or transgenesis) where the polypeptide is translated and processed.

A preferred method of making a soluble derivative of LRP-1 involves a mutant of the wild-type transmembrane domain (e.g., a missense or deletion mutation). For example, a stop codon may be introduced at a site before the transmembrane domain or the polynucleotide portion encoding the transmembrane and cytoplasmic domains may be deleted. A minireceptor comprising cluster II and/or cluster IV may also be synthesized (e.g., by gene splicing or amplifying with adapter primers) and used. An LRP-1 molecule or derivative thereof may be attached to the lipid bilayer of a cellular membrane or another substrate, and then detached/hydrolyzed to make the soluble LRP-1 derivative. For example, a proteolytic enzyme may hydrolyze a peptide bond on the outside of a cell or a lipase may hydrolyze a glycosphingolipid anchor inserted in the lipid bilayer. Alternatively, soluble LRP-1 derivative may be immobilized on a substrate before, during, or after binding to $A\beta$.

Protein fusions may also be made and used. A heterologous or the LRP-1 signal domain may be used for translocation across a cell membrane and transport by the secretory pathway. Soluble LRP-1 derivatives may be glycosylated or otherwise post-translationally modified. A localization domain (e.g., antibody or another member of a binding pair) may be used to increase the local concentration of a soluble LRP-1 derivative in a tissue, organ, or other portion of a subject's body. For example, biotinylation or a fusion with streptavidin may localize the LRP-1 derivative to a body part in/or which the cognate binding member (avidin or biotin, respectively) is attached.

For the receptor-ligand system studied here, LRP-1 ligands (e.g., apoE, apoJ, $\alpha_2M$) and RAP are not required to bind $A\beta$. Soluble LRP-1 derivative may bind free $A\beta$ in solution, or with one of the components in solid phase. After binding between LRP-1 derivative and $A\beta$, either or both may be immobilized on a substrate (e.g., cell, tissue, or artificial solid substrate) at any time before, during, or after binding. The bound complex may be isolated or detected. Candidate compounds to treat Alzheimer's disease may interact with at least one gene, transcript, or protein which is a component of the receptor-ligand system to increase receptor activity (i.e., vascular clearance of $A\beta$), and be screened for their ability to provide therapy or prophylaxis. These products may be used in assays (e.g., diagnostic methods to detect $A\beta$ using sLRP-1) or for treatment; conveniently they are packaged in an assay kit or pharmaceutical form (e.g., single or multiple dose package).

Binding of a soluble LRP-1 derivative with $A\beta$ may take place in solution or on a substrate. The assay format may or may not require separation of bound $A\beta$ from unbound $A\beta$ (i.e., heterogeneous or homogeneous formats). Detectable signals may be direct or indirect, attached to any part of a bound complex, measured competitively, amplified, or any combination thereof. A blocking or washing step may be interposed to improve sensitivity and/or specificity. Attachment of a soluble LRP-1 derivative to a substrate before, after, or during binding results in capture of an unattached species. See U.S. Pat. Nos. 5,143,854 and 5,412,087. Abundance may be measured at the level of protein and/or transcripts of a component of the receptor-ligand system.

A soluble LRP-1 derivative may also be attached to a substrate. The substrate may be solid or porous and it may be formed as a sheet, bead, or fiber. The substrate may be made of cotton, silk, or wool; cellulose, nitrocellulose, nylon, or positively-charged nylon; natural rubber, butyl rubber, silicone rubber, or styrenebutadiene rubber; agarose or polyacrylamide; silicon or silicone; crystalline, amorphous, or impure silica (e.g., quartz) or silicate (e.g., glass); polyacrylonitrile, polycarbonate, polyethylene, polymethyl methacrylate, polymethylpentene, polypropylene, polystyrene, polysulfone, polytetrafluoroethylene, polyvinylidenefluoride, polyvinyl acetate, polyvinyl chloride, or polyvinyl pyrrolidone; or combinations thereof. Optically-transparent materials are preferred so that binding can be monitored and signal transmitted by light. Such reagents would allow capture of $A\beta$ in solution by specific interaction between the cognate molecules and then could immobilize $A\beta$ on the substrate.

A soluble LRP-1 derivative may be attached to a substrate through a reactive group as, for example, a carboxy, amino, or-hydroxy radical; attachment may also be accomplished after contact printing, spotting with a pin, pipetting with a pen, or spraying with a nozzle directly onto a substrate. Alternatively, the soluble LRP-1 derivative may be reversibly attached to the substrate by interaction of a specific binding pair (e.g., antibody-digoxygenin/hapten/peptide, biotin-avidin/streptavidin, glutathione S transferase-glutathione, maltose binding protein-maltose, polyhistidine-nickel, protein A or G/immunoglobulin); cross-linking may be used if irreversible attachment is desired.

Attaching a reporter, which is easily assayed, to a soluble LRP-1 derivative may be used for convenient detection. Reporters include, for example, alkaline phosphatase, $\beta$-galactosidase (LacZ), chloramphenicol acetyltransferase (CAT), $\beta$-glucoronidase (GUS), bacterial/insect/marine invertebrate luciferases (LUC), green and red fluorescent proteins (GFP and RFP, respecttively), horseradish peroxidase (HRP), $\beta$-lactamase, and derivatives thereof (e.g., blue EBFP, cyan ECFP, yellow-green EYFP, destabilized GFP variants, stabilized GFP variants, or fusion variants sold as LIVING COLORS fluorescent proteins by Clontech). Reporters would use cognate substrates that are preferably assayed by a chromogen, fluorescent, or luminescent signal. Alternatively, the soluble LRP-1 derivative may be tagged with a heterologous epitope (e.g., FLAG, MYC, SV40 T antigen, glutathione transferase, hexahistidine, maltose binding protein) for which cognate antibodies or affinity resins are available.

A soluble LRP-1 derivative may be joined to one member of the specific binding pair by genetically ligating appropriate coding regions in an expression vector or, alternatively, by direct chemical linkage to a reactive moiety on the binding member by chemical cross-linking. They may be used as an affinity reagent to identify, to isolate, and to detect interactions that involve specific binding with $A\beta$. This can produce a complex in solution or immobilized to a support.

A soluble LRP-1 derivative may be used as a medicament, diagnostic agent, or used to formulate therapeutic or diagnostic compositions with one or more of the utilities disclosed herein. They may be administered in vitro to a body fluid or tissue in culture, in vivo to a subject's body, or ex vivo to cells outside of the subject that may later be returned to the body of the same subject or another. Fluids and tissues may be further processed after a specimen is taken from the subject's body and before laboratory assay. For example, cells may be diaggregated or lysed, or provided as solid tissue. The specimen may be stored in dry or frozen form prior to assay.

Compounds or derivatives thereof may be used to produce a medicament or other pharmaceutical compositions. Use of compositions which further comprise a pharmaceutically acceptable carrier and compositions which further comprise components useful for delivering the composition to an individual are known in the art. Addition of such carriers and other components to the composition of the invention is well within the level of skill in this art.

The concentration of free Aβ may be decreased by binding to a soluble LRP-1 derivative or removing Aβ bound to a soluble LRP-1 derivative through the body's circulation (e.g., reticuloendothelial system) or by machine (e.g., affinity chromatography, electrophoresis, filtration, precipitation). Efficacy of treatment may be assessed by removal of Aβ from a subject's body or reducing deposition of amyloid in the subject's body. This may be accomplished in an animal model or in a human where the amount and/or the location of may be detected with soluble LRP-1 derivative. It should be noted that the modes of treatment described herein differ significantly from the mechanism described in U.S. Pat. No. 6,156,311 which identifies a role for low-density lipoprotein receptor related protein in endocytosis and degradation of amyloid-β precursor protein (APP).

Labels or other detectable moieties may be attached to soluble LRP-1 derivatives or contrast agents may be included for structural imaging: e.g., X-ray computerized tomography (CT), magnetic resonance imaging (MRI), or optical imaging. Functional imaging such as Single Photon Emission Computed Tomography (SPECT) may also be used. A soluble LRP-1 derivative may be labeled (e.g., gadolinium) for MRI evaluation of amyloid load in the brain or vascular system. A soluble LRP-1 derivative may be labeled (e.g., $^{76}$Br, $^{123}$I) for SPECT evaluation of amyloid load in the brain with a blood-brain barrier (BBB) permeabilizing agent, or for evaluating cerebral amyloid angiopathy with or with the BBB permeabilizing agent.

Reagents may also be provided in a kit for use in performing methods such as, for example: diagnosis, identification of those at risk for disease or already affected, or determination of the stage of disease or its progression. In addition, the reagents may be used in methods related to the treatment of disease such as the following: evaluation whether or not it is desirable to intervene in the disease's natural history, alteration of the course of disease, early intervention to halt or slow progression, promotion of recovery or maintenance of function, provision of targets for beneficial therapy or prophylaxis, comparison of candidate drugs or medical regimens, or determination of the effectiveness of a drug or medical regimen. Instructions for performing these methods, reference values and positive/negative controls, and relational databases containing patient information (e.g., genotype, medical history, disease symptoms, transcription or translation yields from gene expression, physiological or pathological findings) are other products that can be considered aspects of the invention.

The amount and extent of treatment administered to a subject in need of therapy or prophylaxis is effective in treating the affected subject. The invention may be used alone or in combination with other known methods. The individual may be any animal or human. Mammals, especially humans and rodent or primate models of disease, may be treated. Thus, both veterinary and medical methods are contemplated.

A pharmaceutical or diagnostic composition containing one or more soluble LRP-1 derivatives may be administered as a formulation adapted for passage through the blood-brain barrier or direct contact with the endothelium. Alternatively, compositions may be added to the culture medium. In addition to the soluble LRP-1 derivative(s), such compositions may contain physiologically-acceptable carriers and other ingredients known to facilitate administration and/or enhance uptake. (e.g., saline, dimethyl sulfoxide, lipid, polymer, affinity-based cell specific-targeting systems). The composition may be incorporated in a gel, sponge, or other permeable matrix (e.g., formed as pellets or a disk) and placed in proximity to the endothelium for sustained, local release. The composition may be administered in a single dose or in multiple doses which are administered at different times.

A pharmaceutical or diagnostic composition containing one or more soluble LRP-1 derivatives may be administered into the body by any known route. By way of example, the composition may be administered by a mucosal, pulmonary, topical, or other localized or systemic route (e.g., enteral and parenteral). The term "parenteral" includes subcutaneous, intradermal, subdermal, intramuscular, intrathecal, intra-arterial, intravenous, and other injection or infusion techniques, without limitation.

Suitable choices in amounts and timing of doses, formulation, and routes of administration can be made with the goals of achieving a favorable response in the individual with Alzheimer's disease or at risk thereof (i.e., efficacy), and avoiding undue toxicity or other harm thereto (ie., safety). Therefore, "effective" refers to such choices that involve routine manipulation of conditions to achieve a desired effect.

A bolus of one or more soluble LRP-1 derivatives administered into the body over a short time once a day is a convenient dosing schedule. Alternatively, the effective daily dose of soluble LRP-1 derivative(s) may be divided into multiple doses for purposes of administration, for example, two to twelve doses per day. Dosage levels of soluble LRP-1 derivative(s) in a pharmaceutical composition can also be varied so as to achieve a transient or sustained concentration in an individual's body, especially in and around vascular endothelium of the brain, and to result in the desired therapeutic response or protection. But it is also within the skill of the art to start doses at levels lower than required to achieve the desired therapeutic effect and to gradually increase the dosage until the desired effect is achieved. Similarly, dosage levels of soluble LRP-1 derivative(s) in a diagnostic composition may be varied to achieve the desired sensitivity and specificity of detection of Aβ in an individual's body.

The amount of soluble LRP-1 derivative(s) administered is dependent upon factors known to skilled artisans such as its bioactivity and bioavailability (e.g., half-life in the body, stability, and metabolism); chemical properties (e.g., molecular weight, hydrophobicity, and solubility); route and scheduling of administration; and the like. For systemic administration, passage of soluble LRP-1 derivative(s) or metabolite(s) thereof through the blood-brain barrier is important. It will also be understood that the specific dose level to be achieved for any particular individual may depend on a variety of factors, including age, gender, health, medical history, weight, combination with one or more other drugs, and severity of disease.

The term "treatment" of Alzheimer's disease refers to, inter alia, reducing or alleviating one or more symptoms in an individual, preventing one or more symptoms from worsening or progressing, promoting recovery or improving prognosis, and/or preventing disease in an individual who is free therefrom as well as slowing or reducing progression of existing disease. For a given individual, improvement in a symptom, its worsening, regression, or progression may be determined by an objective or subjective measure. Efficacy of treatment may be measured as an improvement in morbidity or mortality (e.g., lengthening of survival curve for a selected population). Prophylactic methods (e.g., preventing or reducing the incidence of relapse) are also considered treatment.

Treatment may also involve combination with other existing modes of treatment (e.g., ARICEPT or donepezil, EXELON or rivastigmine, anti-amyloid vaccine, mental exercise or stimulation). Thus, combination treatment with one or more other drugs and one or more other medical procedures may be practiced.

The amount of soluble LRP-1 derivative(s) which is administered to an individual is preferably an amount that does not induce toxic or other deleterious effects which outweigh the advantages which result from its administration. Further objectives are to reduce in number, diminish in severity, and/or otherwise relieve suffering from the symptoms of the disease as compared to recognized standards of care. The invention may also be effective against neurodegenerative disorders in general: for example, dementia, depression, confusion, Creutzfeldt-Jakob disease, Huntington's disease, Parkinson's disease, loss of motor coordination, multiple sclerosis, stroke, and syncope.

Production of a soluble LRP-1 derivative will be regulated for good laboratory practices (GLP) and good manufacturing practices (GMP) by appropriate governmental regulatory agencies. This requires accurate and comprehensive record-keeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

For therapeutic uses, an appropriate regulatory agency would specify acceptable levels of purity (e.g., lack of extraneous protein and nucleic acids); sterility (e.g., lack of microbes); lack of host cell contamination (e.g., less than 0.5 Endotoxin Units/ml); and potency (e.g., efficiency of gene transfer and expression) for biologics. Another objective may be to ensure consistent and reproducible production of a soluble LRP-1 derivative, which may improve the potency of the biologic while being compatible with the good manufacturing practices used to ensure a pure, sterile, and pyrogen-free product.

The following examples are merely illustrative of the invention, and are not intended to restrict or otherwise limit its practice.

EXAMPLES

It was recently shown that LRP-1 functions as a clearance receptor for Aβ at the blood-brain barrier. LRP-1 -mediated Aβ transcytosis is initiated at the abluminal (brain) site of the endothelium and is therefore directly responsible for eliminating Aβ from brain interstitial fluid into blood. Aβ clearance can be influenced by apoE and $\alpha_2$M, known ligands for LRP-1, but formation of Aβ complexes with either of those ligands have not been shown in the central nervous system (CNS) in vivo during relatively rapid clearance studies (Shibata et al., 2000). Therefore, whether LRP-1 binds directly to free Aβ is determined herein.

The major binding sites of LRP-1 are contained in clusters II and IV of α-subunit which bind most of the currently mapped known ligands of LRP-1, e.g., apoE, $\alpha_2$M, tissue plasminogen activator, plasminogen activator inhibitor-1, APP, factor VIII, and lactoferrin. FIGS. 1A-1B show high affinity binding of soluble monomeric Aβ$_{1-40}$ to immobilized LRP-1 clusters II and IV with K$_d$ values of 0.57±0.12 nM and 1.24±0.01 nM, respectively, determined by the surface plasmon resonance (SPR) analysis. In contrast, Aβ$_{1-42}$ and vasculotropic mutant Aβ (double mutant Dutch/Iowa40 model peptide; Van Nostrand et al., 2001) exhibit greatly reduced binding affinity for LRP-1 clusters II and IV by 6- and 9-fold and 28- and 12-fold, respectively, compared to Aβ$_{1-40}$. The K$_d$ values for Aβ$_{1-42}$ binding to LRP-1 II and IV clusters were 3.00±0.11 nM and 10.10±0.03 nM, respectively, and for mutant Aβ (Dutch/Iowa40) 15.10±0.10 nM and 15.30±0.07 nM, respectively. These data suggest that in vitro LRP-1 preferentially interacts with Aβ$_{1-40}$ compared to Aβ$_{1-42}$ and mutant Aβ.

Binding of all Aβ peptides to LRP-1 clusters II and IV was abolished by RAP, an LRP-1 antagonist (FIGS. 1A-1B). In contrast, the present findings show the affinity of Aβ species to bind to immobilized LRP-1 fragments was greatly reduced by high content of β-sheets in Aβ (FIG. 1C), as determined by the circular dichroism analysis (Zlokovic et al., 1996; Golabek et al., 1996). These results raise a possibility that if LRP-1 is a major clearance receptor for Aβ in the brain, then direct interaction with LRP-1 will mediate preferential clearance of Aβ$_{1-40}$ from brain interstitial fluid (ISF) while favoring the retention of Aβ$_{1-42}$ and mutant Aβ.

According to the amyloid hypothesis, neurotoxic Aβ$_{1-42}$ accumulation in the brain is a major event initiating AD pathogenesis (Hardy and Selkoe, 2002). Increased Aβ$_{1-42}$ accumulation could be associated with increased Aβ production as in familial forms of AD and/or impaired Aβ clearance as in a late-onset AD (Selkoe, 2001; Zlokovic and Frangione, 2003). Increased levels of Aβ in the brain lead to formation of neurotoxic Aβ oligomers and progressive synaptic, neuritic and neuronal dysfunction (Walsh et al., 2002; Dahlgren et al., 2002; Kayed et al., 2003; Gong et al., 2003). Missense mutations within Aβ associate mainly with vascular deposits, as in patients with Dutch mutation (G to C at codon 693, Glu to Gln at position 22) and Iowa mutation (G to A at codon 694, Asp to Asn at position 23). Vasculotropic Dutch (E22Q) or Iowa (D23N) mutant Aβ exhibit enhanced fibrillogenesis and toxicity to cerebral vascular cells, while Dutch/Iowa double mutant Aβ (E22Q,D23N), a model peptide used in the present study, has accelerated pathogenic properties compared to both Dutch and Iowa vasculotropic mutants (Van Nostrand et al., 2001).

To confirm that direct interaction with LRP-1 predisposes to accumulation of Aβ$_{1-42}$ (a mutant Aβ) and clearance of Aβ$_{1-40}$, in vitro clearance of the Aβ species was studied by isolated mouse brain capillaries. FIG. 2A shows rapid saturable uptake of Aβ$_{1-40}$ at the abluminal side of brain capillaries that follows Michaelis-Menten kinetics (Kd=10±2 nM). Uptake of Aβ$_{1-40}$ was abolished by RAP and an anti-LRP-1 antibody suggesting that LRP-1 is involved. Interaction of Aβ$_{1-40}$ with LRP-1 on capillary membranes initiated almost instantaneous internalization of the ligand. Mild acid wash treatment indicated that, after stripping membrane-bound $^{125}$I-Aβ$_{1-40}$, about 80% of Aβ$_{1-40}$ still remains associated with brain capillaries. This suggests a rapid internalization of the ligand within 1 min (FIG. 2B), which is consistent with rapid endocytotic function of the receptor (Li et al., 2001a; 2001b). These data also indicate that binding of reduced Aβ to its carrier proteins apoE and $\alpha_2$M is not required for its brain capillary clearance. However, these Aβ chaperones may still influence Aβ clearance by enhancing its uptake by neurons (Jordan et al., 1998; Qiu et al., 1999) and/or accelerating its extracellular deposition (Golabek et al., 1996).

A series of cross-inhibition experiments using $^{125}$I-labeled Aβ$_{1-40}$ as a test-ligand and different unlabeled Aβ peptides as inhibitors was performed to determine the relative affinity of Aβ species for LRP-dependent brain capillary clearance. The kinetic inhibitory constants K$_i$ determined from the velocity ratios (Zlokovic et al, 1996) revealed that Dutch $A\beta_{1-40}$, wild-type $A\beta_{1-42}$, Dutch $A\beta_{1-42}$ and Dutch/Iowa $A\beta_{1-40}$ exhibit 6, 14, 18 and 22-fold lower affinities for LRP-mediated clearance on brain capillaries than $A\beta_{1-40}$, respectively (FIG. 2C). As for the in vitro binding (FIG. 1C), the affinity of $A\beta$ species for brain capillary clearance was inversely related to the content of β-sheets in $A\beta$ and/or the loss of negative charges caused by mutations within the $A\beta$, i.e., one for Dutch mutant and two for double Dutch and Iowa mutant (Van Nostrand et al., 2001).

Figure 3B:
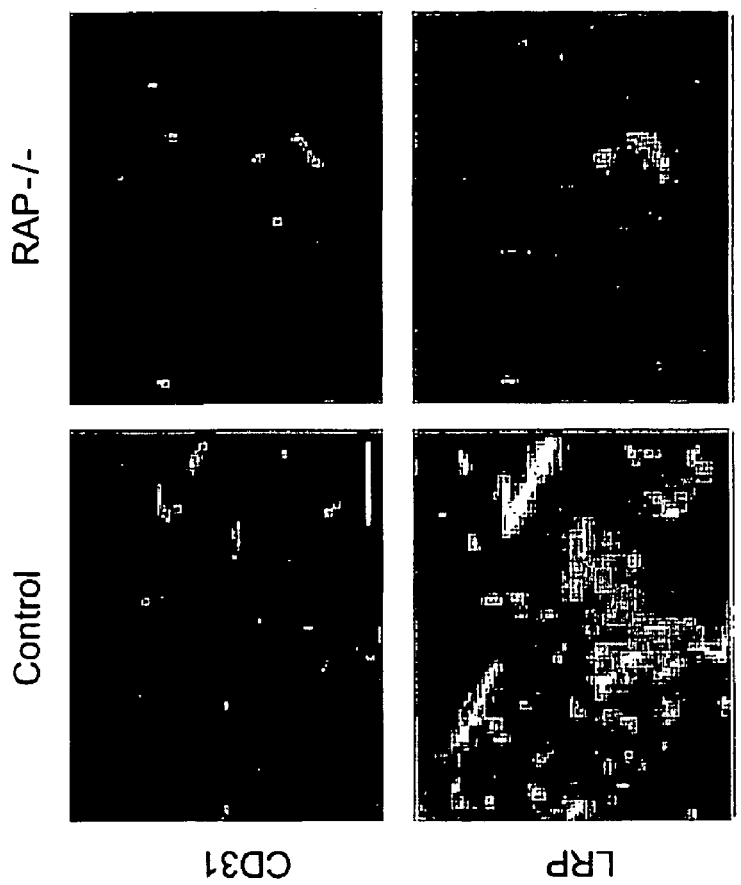
Figure 3A:
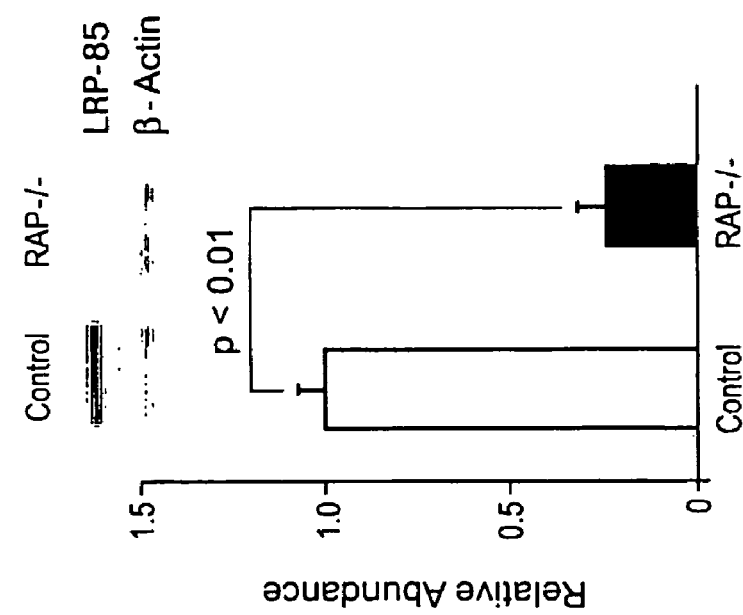
Figure 3D:
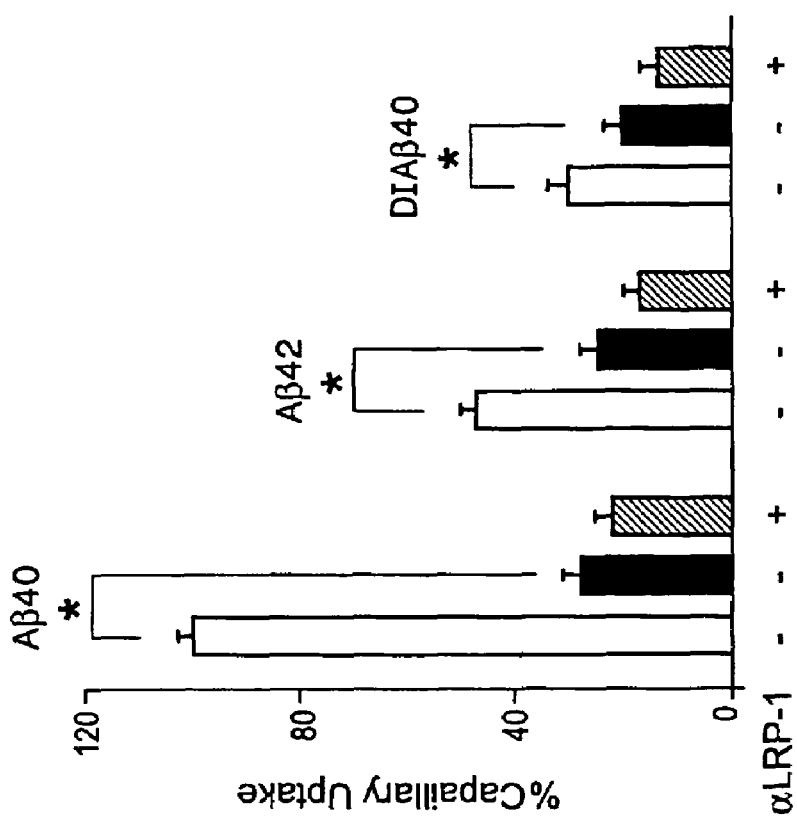
Figure 3C:
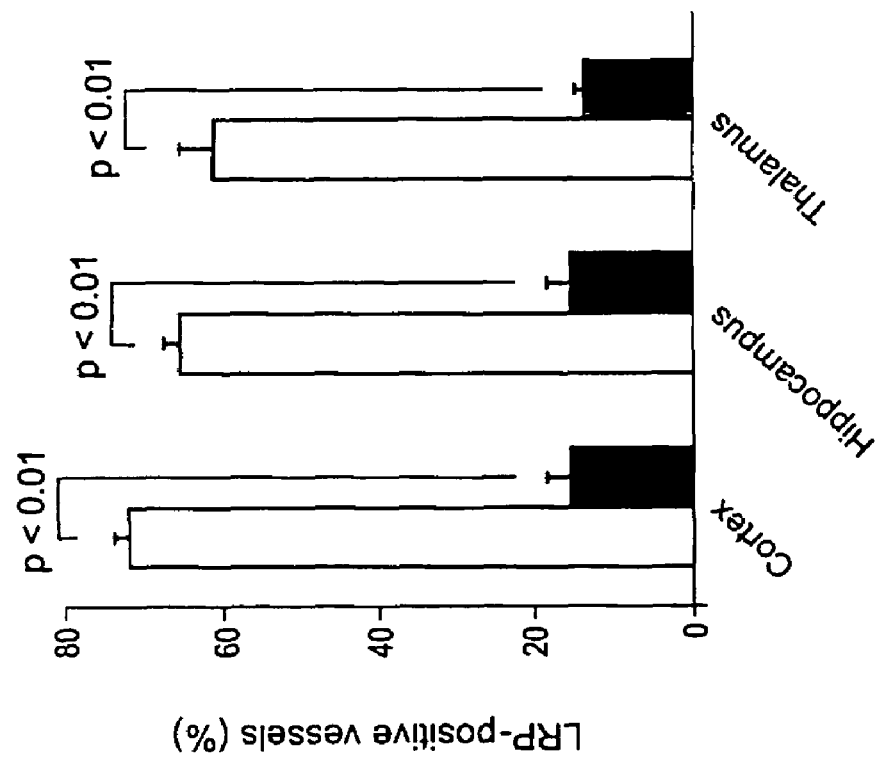

RAP is involved in maintaining proper folding of LRP-1 and preventing its premature interaction with cognate ligands in the endoplasmic reticulum (ER). Deletion of the RAP gene results in substantial reduction in LRP-1 levels in the brain (Van Uden et al., 2002). Here, Western blot analysis (FIG. 3A) and immunostaining of brain tissue in situ (FIG. 3B) showed that the amount of LRP-1 in brain capillaries of RAP null mice was decreased by greater than 75% compared to controls. LRP-positive brain vascular profiles in a RAP null mouse model was reduced in several brain regions, (e.g., cortex, hippocampus and thalamus) from 60% to 70% in controls to 14% to 16% in RAP null mice as indicated by double staining for LRP-1 and endothelial cell marker CD31 (FIG. 3C). To validate LRP-1 as a critical clearance receptor for $A\beta$, clearance of $^{125}$I-labeled $A\beta_{1-40}$, $A\beta_{1-42}$ and mutant $A\beta$ (Dutch/Iowa40) by brain microvessels isolated from RAP null mice and control mice was compared. These results demonstrate that deletion of the RAP gene results in about 80% reduction in vascular clearance of all studied $A\beta$ isoforms in vitro (FIG. 3D). In contrast, deletion of the genes for the LDL receptor or the VLDL receptor did not result in a change in $A\beta$ clearance at the abluminal side of brain capillaries.

Figure 4A:
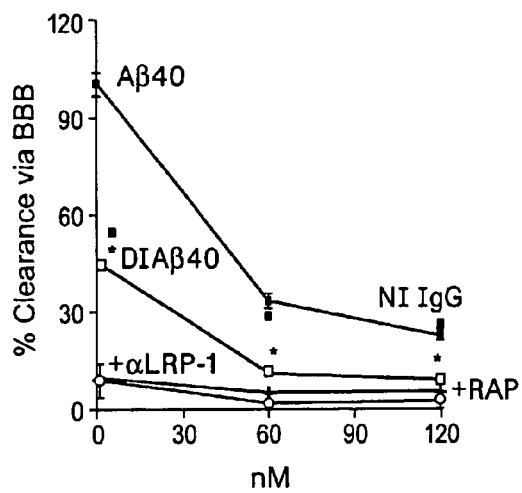

Next, it was determined whether LRP-1 in vivo mediates differential efflux of $A\beta$ peptides across the BBB in mice as it mediates differential $A\beta$ brain capillary clearance in vitro. Transport out of the brain of [$^{125}$I]-labeled $A\beta_{1-40}$, $A\beta_{1-42}$, and mutant $A\beta$ (Dutch/Iowa40) microinfused simultaneously with $^{14}$C-inulin (reference marker) into the mouse brain ISF space was measured (as described Shibata et al., 2000). Clearance of $^{125}$I-labeled $A\beta$ peptides across the BBB was calculated after correction for the passive diffusion of tracers via the ISF bulk flow using the elimination rate of $^{14}$C-inulin. At concentrations comparable to physiological levels of soluble $A\beta$ in brain ISF (i.e., less than or equal to 1 nM) (Cirrito et al., 2003), $A\beta_{1-40}$ wild-type was cleared rapidly from brain across the BBB within few seconds. In contrast, clearance of mutant $A\beta$ (Dutch/Iowa40) was slow and only 40% of the infused peptide was cleared across the BBB within 30 min (FIG. 4A). At higher concentrations, mutant $A\beta$ was almost devoid of clearance at the BBB, while wild-type $A\beta_{1-40}$ exhibited still a substantial clearance. These data are consistent with reduced clearance of mutant $A\beta_{1-40}$ (Dutch) from the cerebrospinal fluid in guinea pigs (Monro et al., 2002) and decreased clearance of mutant $A\beta$ (Dutch/Iowa40) on brain capillaries in vitro observed in this study (FIGS. 2C and 3D). RAP and an anti-LRP-1 antibody, but not non-immune immunoglobulin G (NI IgG in FIG. 4A), almost completely abolished $A\beta$ elimination from brain confirming a critical role of LRP-1 for $A\beta$ clearance from brain in vivo.

Figure 4B:
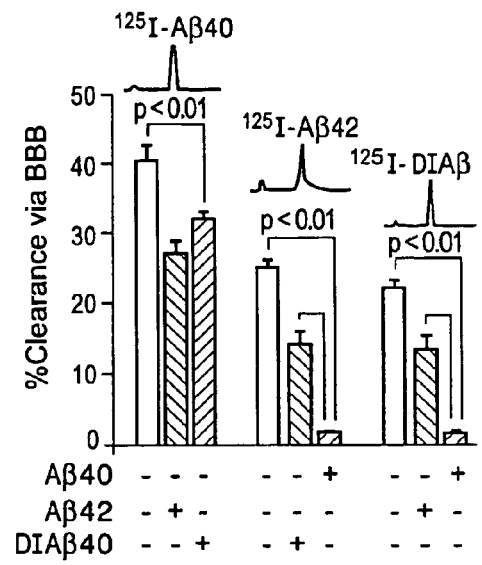
Figure 4C:
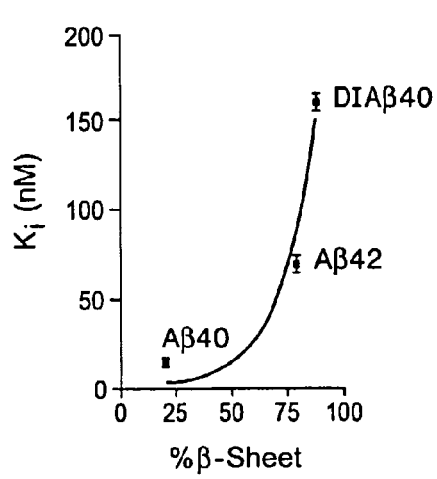

A significant (p<0.05) cross-inhibition of [$^{125}$I]-$A\beta_{1-40}$ clearance at the BBB by unlabeled $A\beta_{1-42}$ and mutant $A\beta$ (Dutch/Iowa40), and a pronounced greater than 95% inhibition of [$^{125}$I]-labeled $A\beta_{1-42}$ and mutant $A\beta$ clearance by unlabeled wild-type $A\beta_{1-40}$ (FIG. 4B), indicated that all $A\beta$ peptides share the same LRP-1-mediated efflux mechanism to exit the brain, and that $A\beta_{1-40}$ exerts a significant retention effect on $A\beta_{1-42}$ and mutant $A\beta$ in vivo. The $K_i$ values determined with $^{125}$I-$A\beta_{1-40}$ as a test-ligand and unlabeled $A\beta$ peptides as inhibitors indicated that the affinity of $A\beta$ for LRP-1-mediated clearance in vivo is remarkably reduced by the high β-sheet content (FIG. 4C). $A\beta_{1-42}$ and mutant $A\beta$ exhibited 8- and 15-fold lower affinity for LRP-1-mediated efflux at the BBB in vivo. All $A\beta$ test-ligands microinfused in brain ISF remained greater than 97% in their monomeric forms as intact peptides during short-term clearance studies within 30 min and over the range of $A\beta$ concentrations less than 100 nM, as reported (Shibata et al., 2000; Zlokovic et al., 2000), and demonstrated by the HPLC analysis (FIG. 4B, insets) and SDS-PAGE analysis of brain homogenates.

To further confirm the role of LRP-1 in rapid efflux of $A\beta$ from the brain in vivo, clearance of $^{125}$I-labeled $A\beta_{1-40}$ and $A\beta_{1-42}$ in RAP null mice was compared to control mice. As expected based on in vitro brain capillary clearance data (FIG. 3D), there was 75% to 85% inhibition of $A\beta_{1-40}$ and $A\beta_{1-42}$ rapid efflux across the BBB in RAP null/severely depleted LRP-1 mice (FIG. 4C). Crossing RAP null mice with APP overexpressing mice doubles the amount of amyloid deposits (Van Uden et al., 2002) which is consistent with the present findings demonstrating that deletion of the RAP gene almost completely eliminates rapid $A\beta$ clearance at the BBB.

Figure 4D:
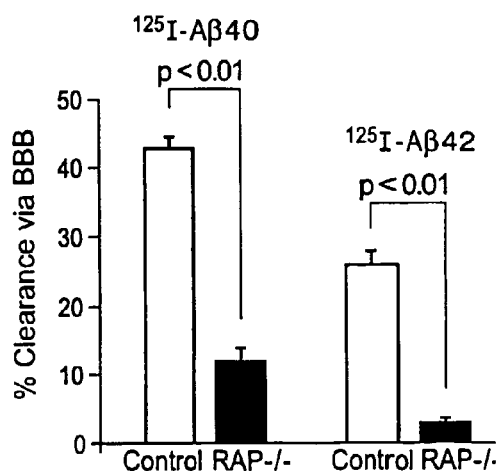

To validate the clearance hypothesis for endogenous $A\beta$, accumulation of $A\beta$ in transgenic Dutch/Iowa (Tg-DI) mice expressing low levels of human APP under the control of a Thy 1.2 neuronal promoter harboring the Dutch and Iowa vasculotropic mutations were compared to Tg-2576 APP overexpressing mice (Hsiao et al., 1996). Tg-DI mice produce mutant $A\beta$ (Dutch/Iowa) that compared to the wild-type $A\beta_{1-40}$ binds to LRP-1 with significantly lower affinity (FIGS. 2B-2C) and exhibits low LRP-1-clearance on brain capillaries (FIGS. 2B and FIG. 3D) and across the BBB (FIGS. 4A and 4D). At 3, 6 or 12 months of age, the level of APP in the brain of Tg-DI mice was considerably lower than in Tg-2576 mice, as determined by the quantitative immunoblot analysis of brain homogenates (FIGS. 5A-5B). Despite about 24-fold lower levels of human APP (FIG. 5B), the Tg-DI mice still exhibited robust brain accumulations of mutant $A\beta$ earlier than Tg-2576 mice overproducing wild-type $A\beta$ (FIG. 5C), i.e., by 15- and 5-fold higher for the $A\beta_{1-40}$ and $A\beta_{1-42}$ isoforms, respectively, at 6 months of age.

Consistent with early accumulation of $A\beta$, Tg-DI mice developed early $A\beta$ plaque-like deposits in the cortex and hippocampus at 3 months of age (FIG. 5D, left), while Tg-2576 mice initially presented $A\beta$ deposits at about 9 months of age, as reported (Hsiao et al., 1996; Kawarabayashi et al., 2001). The $A\beta$ plaque-like deposits in Tg-DI mice were abundant at 12 months (FIG. 5D, right), but the majority presented as diffuse plaques similar as in patients with the Dutch and Iowa $A\beta$ mutations. Significant intracerebral vascular association of $A\beta$ in Tg-DI mice (FIG. 5E) was suggestive of a clearance problem at the level of brain's blood vessels, consistent with prominent cerebrovascular pathology in Dutch and Iowa patients (Vinters and Farag, 2003). Plasma levels of mutant $A\beta$ in Tg-DI mice were extremely low, i.e., less than 25 μM, corroborating low efflux of mutant $A\beta$ from brain (FIGS. 4A and 4D). In Tg-2576 mice, the ratio of $A\beta_{1-42}$:$A\beta_{1-40}$ in plasma was 1:10, while the ratio in brain varied between 1:3 to 1:2 at 6 and 12 months of age, respectively (FIG. 5C). These results suggest lower clearance of endogenous $A\beta_{1-42}$ relative to $A\beta_{1-40}$, as would be expected from substantially lower LRP-1-mediated clearance of exogenous $A\beta_{1-42}$ by brain capillaries (FIGS. 2B and 3D) and across the BBB (FIGS. 4B-4D).

Increased fibrillogenic properties of mutant Aβ observed in vitro (Van Nostrand et al., 2001) may contribute to its decreased clearance from brain in vivo. However, the presence of mainly non-fibrillar Aβ parenchymal deposits in Tg-DI mice within the first 12 months of age would argue against the possibility that enhanced fibrillogenicity is the primary mechanism for reduced efflux of endogenous mutant Aβ from brain. To better understand the relationship between brain capillary LRP-1 and accumulation of AB, the expression of LRP-1 in brain microvessels in situ was next studied in Tg-DI and Tg-2576 mice. Surprisingly double immunostaining for brain endothelial LRP-1 and endothelial cell marker CD31 indicated substantial reduction of LRP-1-positive vascular profiles in several brain regions in Tg-DI and Tg-2576 mice, i.e., only 5% to 20% and 25% to 30% of microvessels in 4- to 6-month old Tg-DI and Tg-2576 mice were positive for LRP-1, respectively, compared to 65% to 75% in age-matched littermate controls (FIG. 5F). The decrease in LRP-1 vascular profiles at 12 months of age was also more pronounced in Aβ-accumulating transgenic mice than in controls (FIG. 5G). A significant age-dependent decrease of LRP-1 at the BBB was consistent with reported down-regulation of LRP-1 in the brain during normal aging. The most obvious early reductions observed in LRP-1 expression at the BBB in Tg-DI mice at 4 months to 6 months of age correlated well with significantly higher Aβ accumulation in these mice relative to Tg-2576 mice (FIG. 5C).

The present study reveals that direct interaction between LRP-1 and Aβ in brain endothelium may critically influence neurotoxic and vasculotropic Aβ accumulations by promoting retention of Aβ species with high β-sheet content and genetic mutations within Aβ while clearing soluble $A\beta_{1-40}$. Mutations within Aβ do not significantly affect the affinity of mutant Aβ to bind to sLRP-1 cluster II or cluster IV. In contrast to LRP-1, the receptor for advanced glycation end-products (RAGE) mediates continuous influx of circulating Aβ into the brain and is overexpressed in brain vasculature in transgenic APP models and in AD (Deane et al., 2003). There is a possibility that increased activity of LRP-1 receptor at the blood-brain barrier or in the vascular system will reduce levels of Aβ in the CNS by acting directly to free Aβ. Applications include subjects with familial forms of Alzheimer's disease (FAD) with cerebral amyloid angiopathy (CAA), such as patients with Dutch or Iowa mutations (FAD/CAA). Because the LRP-1 cluster II or IV domain binds efficiently to wild-type and mutant Aβ, they can be used for diagnostic purposes in Alzheimer's disease, FAD/CM, and Down syndrome as imaging agents in the brain to visualize changes associated with vascular pathology.

Since soluble LRP-1 derivatives bind Aβ, they can be used to promote egress of Aβ from brain into blood. The levels of Aβ free and bound to soluble LRP-1 derivative can be used to develop a double sandwich ELISA diagnostic blood test in Alzheimer's disease, FAD/CM, and Down syndrome. The mechanism of action may be sequestration of circulating wild-type or mutant Aβ over hours or days, similar to other peripheral Aβ-binding agents such as anti-Aβ antibody, gelsolin, GM1, and sRAGE. Using a brain perfusion model (Deane et al., 2003), it was shown that either sLRP-1 cluster II or cluster IV sequesters Aβ in the systemic circulation, and prevents Aβ transport across the blood-brain barrier into the brain. In contrast to other Aβ-binding agents, use of one or more soluble LRP-1 derivatives provides the advantages that (1) they should be well-tolerated by a subject and avoids an immune or neuroinflammatory response in the brain and cerebral blood vessels, which can be a serious complication of anti-Aβ antibody therapy, and (2) their binding affinities for Aβ is much higher than gelsolin, GM1, or sRAGE.

These properties of soluble LRP-1 derivatives can also be used to lower the level of Aβ in the brain of transgenic Alzheimer's disease mice, transgenic FAD/CAA mice, or Alzheimer's disease and FAD/CAA patients by sequestering Aβ over long periods of time (e.g., months, years) and possibly in the CNS itself. For this purpose, one or more soluble LRP-1 derivatives can be used alone, or in combination with agents that permeabilize the blood-brain barrier (e.g., insulin-like growth factor-1, RMP-7), neuroprotective agents (e.g., activated protein C as described in Guo et al., 2004), or other therapies to lower Aβ in an individual: immunization or vaccination against Aβ; administration of ganglioside, gelsolin, or sRAGE; inhibiting beta/gamma secretase-mediated processing of amyloid precursor protein; osmotic opening of the blood-brain barrier (Neuwelt et al., 1985); normalization of cerebrospinal fluid production (Silverberg et al., 2003); or combinations thereof.

MATERIALS AND METHODS

Reagents

Wild-type and mutant Aβ (Dutch40, Dutch42, Dutch/Iowa40) peptides were synthesized, by solid-phase F-moc (9-fluorenylmethoxycarbonyl) amino acid synthesis, purified by reverse phase-HPLC and structurally characterized (as described in Burdick et al., 1992; Van Nostrand et al., 2001). Recombinant LRP-1 fragments encompassing clusters II and IV were produced using stable transfected baby hamster kidney cell lines (as described in Westein et al., 2002). Human recombinant RAP (EMD Biosciences, San Diego, CA.), polyclonal goat anti-human LRP-1 N20 antibody which cross reacts with mouse LRP-1 (1:200, Santa Cruz Biotech, Santa Cruz, CA.), monoclonal mouse antibody against C-terminal domain of human LRP-1 β-chain which cross reacts with mouse LRP-1 (5A6, 1:350, 5 µg/ml; EMD Biosciences, San Diego, CA.), monoclonal mouse antibody against human LRP-1 α-chain (8G1,1 :240, 5 µg/ml; EMD Biosciences, San Diego, CA.), monoclonal mouse antibody (mAβ) P2-1 specific for human APP (1:1000, 1 mg/ml), mAβ 22C11 which recognizes mouse and human APP (1:100, 0.5 mg/ml; Chemicon International, Temecula, CA.), mAβ 66.1 to residues 1-8 of human Aβ (1:1000,1 mg/ml) (Deane et al., 2003), rat anti-mouse CD31 antibody (1:200, BD Pharmigen, Lexington, Ky.) and polyclonal rabbit antibody to human von Willebrand Factor, vWF (1:200, DAKO, Carpinteria, CA.) were used.

Surface Plasmon Resonance Analysis

LRP-1 clusters II and IV were immobilized at CM5 chips at a density of 10-20 fmol/mm$^2$ and incubated with $A\beta_{1-40}$, $A\beta_{1-42}$, and mutant Aβ (Dutch/Iowa40) (0 nM to 50 nM) in 150 mM NaCl, 0.005% (v/v) TWEEN surfactant and 25 mM HEPES buffer (pH 7.4) at a flow rate of 5 µl/min for 2 min at 25° C. (as described in Westein et al., 2002). RAP was used at 500 nM. Ligand solution was replaced with buffer to initiate dissociation. The data were analyzed to calculate apparent association rate constants $k_{on(app)}$ and apparent dissociation rate constants $k_{off(app)}$ using a single-site binding model (as described in Westein et al., 2002). Apparent affinity constants $K_{d(app)}$ were inferred from the ratio $k_{off(app)}/k_{on(app)}$. Data are based on three to five measurements using six to nine different concentrations for each measurement. Data are presented as the mean±SEM. Analysis was performed using BIACORE X biosensor system (Uppsala, Sweden) and BIA evaluation 3.0 software (Biocore, Sweden).

Secondary Structure Analysis

Secondary structure of peptides was analyzed by circular dichroism (as described in Zlokovic et al., 1996 and Golabek et al., 1996). Briefly 20 μg to 25 μg of hexafluoroisopropanol treated seedless peptide was initially dissolved in 980 μl of 10 mM phosphate buffer, pH 7.4, and centrifuged to remove any precipitated or undissolved material. The CD spectrum was recorded within 24 hr (corresponding to the time of peptides use for in vitro and in vivo assays) using a 1 mm path length cell in an Aviv 202 CD spectrometer (Proterion, Piscataway, N.J.). Results are expressed as molar ellipticity and the percentage of α-helix, β-sheet, β-turn and random coil determined for each peptide. Under the present conditions, there was neither formation of high molecular weight oligomers, as confirmed by gel exclusion chromatography and dot blots with oligomer-specific antibodies (as described in Kayed et al., 2003), nor fibrillar and aggregated forms, as confirmed by atomic force microscopy.

Radioiodination of Aβ

Radioiodination of Aβ peptides was carried out using a mild lactoperoxidase method. Typically 10 μg of Aβ was labeled for 18 min at room temperature with 2 mCi of Na[$^{125}$I]. After radiolabeling, preparations were processed by reverse-phase HPLC using a Vydac C4 column and a 30 min linear gradient of 25% to 40% acetonitrile in 0.059% trifluoroacetic acid to separate the monoiodinated non-oxidized form of Aβ (which is the tracer being used) from diiodinated Aβ, non-labeled non-oxidized Aβ, and oxidized Aβ species. The material in the peaks eluted from HPLC was determined by MALDI-TOF mass-spectrometry to ensure the purity of the radiolabeled species. For MALDI-TOF mass spectrometry, Aβ peptides were labeled under identical conditions using Na[$^{127}$I] instead of the radioactive nuclide. Typically the specific activities obtained with this protocol were in the range of 45 to 65 μCi/μg of peptide. Rapid radiolysis of Aβ is possible and, therefore, the quality of each preparation was rigorously monitored. For brain capillary uptake studies and animal clearance studies, in most experiments the preparations were used within 24 hr of labeling such that greater than 99% was TCA precipitable. If used within 72 hr of labeling, the radiolabeled peptides were stabilized in ethanol as a quenching agent. Prior to in vitro study or infusion into animals, HPLC purification of the tracer was performed. HPLC/SDS-PAGE analysis was used to confirm the monomeric state of infused radiolabeled Aβ. The secondary structure of Aβ remained unchanged by iodination as confirmed by CD analysis.

Brain Capillary Uptake

To study uptake at the abluminal brain side of capillaries, capillaries from wild-type mice and RAP null mice were isolated from brain using a modified procedure (as described in Wu et al., 2003). Brain capillaries were incubated with $^{125}$I-labeled Aβ$_{1-40}$, Aβ$_{1-42}$ and mutant Aβ (Dutch/Iowa40) at concentration of 1 nM in mock CSF at 37° C. for 1 min. Incubation medium contained 1 mM sodium perchlorate to prevent free iodide uptake. Self- and cross-inhibition studies were performed with unlabeled Aβ$_{1-40}$ from 1 nM to 120 nM, unlabeled Aβ$_{1-42}$ or mutant Aβ (Dutch40, Dutch42, Dutch/Iowa40) at 40 nM, RAP at 500 nM, and LRP-1-specific polyclonal N20 antibody at 60 μg/ml. Ice-cold stop/strip solution (0.2 M acetic acid, pH 2.6, 0.1 M NaCl), was added to one set of experiments as a mild acid wash to strip membrane-bound Aβ and estimate the amount of Aβ that was internalized (as described in Melman et al., 2002).

Brain Clearance Studies

All studies were performed according to National Institutes of Health guidelines using an approved institutional protocol. CNS clearance of $^{125}$I-Aβ$_{1-40}$, $^{125}$I-mutant Aβ (Dutch/Iowa40) and $^{125}$I-Aβ$_{1-42}$ was determined simultaneously with $^{14}$C-inulin (reference marker) in male C57BL/6 mice, RAP null mice and littermate controls 8-10 weeks old (as described in Shibata et al., 2000). Briefly a stainless steel guide cannula was implanted stereotaxically into the right caudate-putamen of anesthetized mice (0.5 mg/kg ketamine and 5 mg/kg xylazine I.P.). Coordinates for tip of the cannula were 0.9 mm anterior and 1.9 mm lateral to the bregma and 2.9 mm below the surface of the brain. Animals were allowed to recover after surgery prior to radiotracer studies. Clearance experiments were performed before substantial chronic processes have occurred, as assessed by histological analysis of negative tissue staining for astrocytes (glial fibrillar acidic protein) and activated microglia (antiphosphotyrosine), but allowing time for repair of the BBB to large molecules, that was typically 4 hr to 6 hr after the cannula insertion (Cirrito et al., 2003). Tracer fluid (0.5 μl) containing [$^{125}$I]-Aβ and $^{14}$C-inulin (reference molecule) was injected over 5 min via an ultramicropump with a MICRO4 controller (World Precision Instruments, Sarasota, Fla.) into brain ISF. When the effects of the different unlabeled molecular reagents were tested, they were injected simultaneously with radiolabeled ligands. For self-inhibition studies, the uptake of $^{125}$I-Aβ$_{1-40}$ and $^{125}$I-mutant Aβ (Dutch/Iowa40) was studied over a range of carrier concentrations from 0.5 nM to 120 nM. For cross-inhibition studies, efflux of $^{125}$I-test-peptides was studied at a carrier concentration of 40 nM and the inhibitory concentration of unlabeled Aβ peptides at 120 nM. Brain and blood were sampled 30 min after tracers injection and prepared for radioactivity analysis by TCA, HPLC and SDS-PAGE/immunoprecipitation analysis to determine the molecular forms of test-tracers. Gamma counting for $^{125}$I-radioactivity was performed using WALLAC VIZARD gamma counter (Perkin Elmer, Meriden, Conn.) and beta-counting for $^{14}$C-inulin using a TRI-CARB 2100 liquid scintillation counter (Perkin Elmer), Meriden, Conn. Previous studies with $^{125}$I-labeled Aβ peptides demonstrated an excellent correlation between TCA and HPLC methods. $^{125}$I-labeled Aβ$_{1-40}$, Aβ$_{1-42}$ or mutant Aβ (Dutch/Iowa40) injected into the brain ISF was greater than 99% intact by TCA/HPLC analysis. The Aβ standards eluted between 29.1 and 31.2 min for different Aβ peptides. For SDS-PAGE analysis, TCA precipitated samples were resuspended in 1% SDS, vortexed and incubated at 55° C. for 5 min, then neutralized, boiled for 3 min, homogenized, and analyzed by electrophoresis in 10% Tris-Tricine gels followed by fluorography. These methods have been previously described (Zlokovic et al., 1996; Shibata et al., 2000; Deane et al., 2003).

Calculations $^{125}$I-Aβ brain capillary uptake was corrected for the distribution of $^{14}$C-inulin (extracellular space marker) and determined as the tissue to medium ratio as: c.p.m. for TCA-precipitable $^{125}$I-radioactivity (mg capillary protein)/c.p.m. for TCA-precipitable $^{125}$I-radioactivity (ml medium) (1) (as described in Shibata et al., 2000). Briefly the percentage of radioactivity remaining in the brain after microinjection was determined as % recovery in brain $=100 \times (N_b/N_i)$ (2), where, $N_b$ is the radioactivity remaining in the brain at the end of the experiment and $N_i$ is the radioactivity injected into the brain ISF, i.e., the d.p.m. for $^{14}$C-inulin and the c.p.m. for TCA-precipitable $^{125}$I-radioactivity (intact Aβ). The percentage of Aβ cleared through the BBB was calculated as $[(1-N_{b(A\beta)}/$ $N_{i(A\beta)})-(1-N_{b(inulin)}/N_{i(inulin)})]\times100$, using a standard time of 30 min (3). Efflux of Aβ from brain ISF via transport across the BBB at different concentrations of peptides, $J_{out}$, was calculated as $[(1-N_{b(A\beta)}/N_{i(A\beta)})-(1-N_{b(inulin)}/N_{i(inulin)})]/T \times C_{A\beta}$ (4) where $C_{A\beta}$ is Aβ concentration in the infusate. The half-saturation concentration for Aβ elimination via BBB transport, $K_m$, was calculated from $J_{out}=CI_{max}/(K_m+C_{A\beta})$ (4), where $CI_{max}$ (pmol/s/L ISF) represents the maximal efflux capacity for the saturable Aβ efflux across the BBB corrected for the rate of ISF flow. The $K_m$ value for Aβ$_{1-40}$ uptake by isolated brain capillaries was calculated using Michaelis-Menten analysis. The inhibitory constants, $K_i$, were calculated from the velocity ratios (Zlokovic et al., 1996) as $K_i = (J_i \times K_m \times C_i)/(J_{out}-J_i)(K_m+C_{A\beta40})$, where $C_i$ and $C_{A\beta40}$ were the inhibitory concentrations of test-Aβ peptide and Aβ$_{1-40}$ in the infusate in vivo or incubation medium in vitro. Kinetic constants were obtained by a non-linear regression curve fitting (PRISM 3.0 software).

Transgenic Mice

Tg-2576 mice in a C57BL6/SJL background (Hsiao et al., 1996) and Tg-DI (Dutch/Iowa) mice in C57BL/6 background (Davis et al., unpublished observations) were used. Human APP (770 isoform) cDNA harboring the Swedish (KM670/671NL), Dutch (E693Q), and Iowa (D694N) mutations was subcloned between exons II and IV of a Thy-1.2 expression cassette (a gift from Dr. F. LaFerla, University of California, Irvine). The 9 kb transgene was liberated by NotI/PvuI digestion, purified, and microinjected into pronuclei of C57BL/6 single-cell embryos at the Stony Brook Transgenic Mouse Facility. Founder transgenic mice were identified by Southern blot analysis of tail DNA. Transgenic offspring were determined by PCR analysis of tail DNA using the following primers for human APP to generate a 500 base pair product.

Quantification of AB

Soluble and insoluble pools of Aβ peptides were determined by ELISA of carbonate extracted forebrain tissue arid of guanidine lysates of the insoluble pellets resulting from the carbonate extracted brain tissue, respectively (DeMattos et al., 2002b). Levels of total Aβ were compared between Tg-2576 and Tg-DI mice.

Histological Analysis

For neuropathological analysis on mouse brain tissue in Tg-2576 and Tg-DI mice, tissue sections were cut from mouse brain hemispheres in the sagittal plane either at 5 μm (paraffin embedded fixed tissue) or 14 μm (fresh frozen tissue). Aβ immunoreactive deposits were identified with human specific monoclonal mouse antibody 66.1 to Aβ (Deane et al., 2003). For LRP-1 staining on brain microvessels in RAP null, Tg-2576, Tg-DI, and wild-type mice, 14 μm frozen acetone-fixed tissue sections were double immunostained for LRP-1 and CD31 (endothelial marker). LRP-1-specific IgG (5A6) was used as a primary antibody. Biotinylated anti-mouse IgG was used as a secondary antibody and was detected with fluoresceinated streptavidin (1:1000, Vector Laboratories, Burlingame, CA). M.O.M kit (Vector Laboratories, Burlingame, CA) was used to block endogenous IgG (as described in Sata et al., 2002). For CD31 staining, mouse CD31-specific IgG was used as a primary antibody, and Alexa Fluor 594 donkey anti-rat IgG (1:500, Molecular Probes, Eugene, OR.) as a seconddary antibody.

Human Brain Endothelial Cells

Human brain endothelial cells (BEC) were isolated from rapid autopsies of neurologically normal young individuals after trauma. BECs were characterized and cultured (as described in Cheng et al., 2003) and incubated with different Aβ isoforms at concentrations ranging from 1 nM to 20 μM within 48 hr. Cells were lysed and equal amounts of proteins electrophoresed (10 μg/ml) on 10% SDS-polyacrylamide gel, transferred onto nitrocellulose membrane and probed with 5A6 (β-chain) or 8G1 (α-chain) human anti-LRP-1-specific IgGs. The relative density of each protein was determined by scanning densitometry using β-actin as an internal control.

Metabolic Labeling

Human BEC ($4 \times 10^5$) were pulsed for 1 hr at 37° C. with 400 μCi of [$^{35}$S]-methionine (greater than 1000 Ci/mmol; Perkin Elmer Life Science, Boston, Mass.) in methionine-free Dulbecco modified Eagle medium (GIBCO BRL, New York, N.Y.) (as described in Guenette et al., 2002). Cells were chased at the indicated times within 48 hr. Cell lysates were immunoprecipitated with anti-LRP-1 515 kDa α-chain specific IgG (8G1) on SDS-PAGE. The intensity of signal was quantified in pixels using Storm 860 PhosphorImager (Amersham Biosciences, Piscataway, N.J.).

Statistical Analysis

Data were analyzed by multifactorial analysis of variance, Student's t-test, and Dunnett's t test.

REFERENCES

Burdick et al. (1992) Assembly and aggregation properties of synthetic Alzheimer's A4/β amyloid peptide analogs. J. Biol. Chem. 267:546-554.

Cheng et al. (2003) Activated protein C blocks p53-mediated apoptosis in ischemic human brain endothelium and is neuroprotective. Nature Med. 9:338-342.

Cirrito et al. (2003) In vivo assessment of brain interstitial fluid with microdialysis reveals plaque-associated changes in amyloid-β metabolism and half-life. J. Neurosci. 23:8844-53.

Dahlgren et al. (2002) Oligomeric and fibrillar species of amyloid-β peptides differentially affect neuronal viability. J. Biol. Chem. 277:32046-32053.

Deane et al. (2003) RAGE mediates amyloid-β transport across the blood-brain barrier and accumulation in brain. Nature Med. 9:907-913.

DeMattos et al. (2002a) Brain to plasma amyloid-Aβ efflux: A measure of brain amyloid burden in a mouse model of Alzheimer's disease. Science. 295:2264-2267.

DeMattos et al. (2002b) Clusterin promotes amyloid plaque formation and is critical for neuritic toxicity in a mouse model of Alzheimer's disease. Proc. Natl. Acad. Sci. USA 99:10843-10849.

Golabek et al. (1996) The interaction between apolipoprotein E and Alzheimer's amyloid beta-peptide is dependent on beta-peptide conformation. J Biol. Chem. 271:10602-10606.

Gong et al. (2003) Alzheimer's disease-affected brain: Presence of oligomeric Aβ ligands (ADDLs) suggests a molecular basis for reversible memory loss. Proc. Natl. Acad. Sci. USA 100:10417-10422.

Guenétte et a. (2002) Low-density lipoprotein receptor-related protein levels and endocytic function are reduced by overexpression of the FE65 adaptor protein, FE65L1. J. Neurochem. 82:755-762.

Guo et al. (2004) Activated protein C prevents neuronal apoptosis via protease activated receptors 1 and 3. Neuron 41:563-572.

Hardy and Selkoe (2002) The amyloid hypothesis of Alzheimer's disease: Progress and problems on the road to therapeutics. Science. 297:353-356.

Herz and Strickland (2001) LRP: A multifunctional scavenger and signaling receptor. J. Clin. Invest. 108:779-784.

Herz et al. (1988) Surface location and high affinity for calcium of a 500-kd liver membrane protein closely related to the LDL-receptor suggest a physiological role as lipoprotein receptor. EMBO J. 7:4119-4127

Hsiao et al. (1996) Correlative memory deficits, Aβ elevation, and amyloid plaques in transgenic mice. Science 274: 99-102.

Jordán et al. (1998) Isoform-specific effect of apolipoprotein E on cell survival and β-amyloid-induced toxicity in rat hippocampal pyramidal neuronal cultures. J. Neurosci. 18:195-204.

Kang et al. (1997) Genetic association of the low-density lipoprotein receptor-related protein gene (LRP), an apolipoprotein E receptor, with late-onset Alzheimer's disease. Neurology 49:56-61.

Kang et a. (2000) Modulation of amyloid β-protein clearance and Alzheimer's disease susceptibility by the LDL receptor-related protein pathway. J. Clin. Invest. 106:1159-1166.

Kawarabayashi et al. (2001) Age-dependent changes in brain, CSF, and plasma amyloid Aβ protein in the Tg2576 transgenic mouse model of Alzheimer's Disease. J. Neuroscience. 21:372-381.

Kayed et al. (2003) Common structure of soluble amyloid oligomers implies common mechanism of pathogenesis. Science 300:486-489.

Kounnas et al. (1995) LDL receptor-related protein, a multifunctional ApoE receptor, binds secreted beta-amyloid precursor protein and mediates its degradation. Cell 82:331-340.

Li et al. (2001a) Differential functions of members of the low density lipoprotein receptor family suggested by their distinct endoytosis rates. J. Biol. Chem. 276:18000-18006.

Li et al. (2001b) Identification of a major cyclic AMP-dependent protein kinase A phosphorylation site within the cytoplasmic tail of the low-density lipoprotein receptor-related protein: Implication for receptor-mediated endocytosis. Mol. Cell. Biol. 21:1185-1195.

Matsuoka et al. (2003) Novel therapeutic approach for the treatment of Alzheimer's disease by peripheral administration of agents with an affinity to Aβ-amyloid. J Neurosci. 23:29-33.

Melman et al. (2002) Proteasome regulates the delivery of LDL receptor-related protein into the degradation pathway. Mol. Biol. Cell 13:3325-3335.

Monro et al. (2002) Substitution at codon 22 reduces clearance of Alzheimer's amyloid-beta peptide from the cerebrospinal fluid and prevents its transport from the central nervous system into blood. Neurobiol. Aging 23:405-412.

Narita et al. (1997) $\alpha_2$-Macroglobulin complexes with and mediates the endocytosis of β-amyloid peptide via cell surface low-density lipoprotein receptor-related protein. J. Neurochem. 69:1904-1911.

Neuwelt et al. (1985) Osmotic blood-brain barrier modification: Monoclonal antibody, albumin, and methotrexate delivery to cerebrospinal fluid and brain. Neurosurgery 17:419-423.

Pietrzik et al. (2002) The cytoplasmic domain of the LDL receptor-related protein regulates multiple steps in APP processing. EMBO. J. 21:5691-5700.

Qiu et al. (1999) $\alpha_2$-Macroglobulin enhances the clearance of endogenous soluble β-amyloid peptide via low-density lipoprotein receptor-related protein in cortical neurons. J. Neurochem. 73:1393-1398.

Sata et al. (2002) Hematopoietic stem cells differentiate into vascular cells that participate in the pathogenesis of atherosclerosis. Nature Med. 8:403-409.

Selkoe (2001) Clearing the brain's amyloid cobwebs. Neuron 32:177-180.

Shibata et al. (2000) Clearance of Alzheimer's amyloid-$A\beta_{1-40}$ peptide from brain by low-density lipoprotein receptor-related protein-1 at the blood-brain barrier J. Clin. Invest. 106:1489-1499.

Silverberg et al. (2003) Alzheimer's disease, normal-pressure hydrocephalus, and senescent changes in CSF circulatory physiology: A hypothesis. Lancet Neurol. 2:506-511.

Ulery et al. (2000) Modulation of β-amyloid precursor protein processing by the low density lipoprotein receptor-related protein (LRP). Evidence that LRP-1 contributes to the pathogenesis of Alzheimer's Disease. J. Biol. Chem. 275: 7410-7415.

Van Nostrand et al. (2001) Pathogenic effects of D23N Iowa amyloid β-protein. J. Biol. Chem. 276:32860-32866.

Van Uden et al. (2002) Increased extracellular amyloid deposition and neurodegeneration in human amyloid precursor protein transgenic mice deficient in receptor-associated protein. J. Neurosci. 22:9298-9304.

Vinters and Farag (2003) Amyloidosis of cerebral arteries. Adv. Neurol. 92:105-112.

Walsh et al. (2002) Naturally secreted oligomers of amyloid β protein potently inhibit hippocampal long-term potentiation in vivo. Nature 416:535-539.

Westein et al. (2002) The α-chains of C4b-binding protein mediate complex formation with low density liporpoprotein receptor-related protein. J. Biol. Chem. 277:2511-2516.

Wu et al. (2003) A simple method for isolation and characterization of mouse brain microvascular endothelial cells. J. Neurosci. Meth. 130:53-63.

Zerbinatti et al. (2004) Increased soluble amyloid B peptide and memory deficits in amyloid model mice overexpressing the LDL receptor-related protein. Proc. Natl. Acad. Sci. USA 101:1075-1080.

Zlokovic and Frangione (2003) Transport-clearance hypothesis for Alzheimer's disease and potential therapeutic implications. Aβ Metabolism in Alzheimer's Disease. Ed. T. Saido (Landes Bioscience) 114-122.

Zlokovic et al. (1996) Glycoprotein 330/megalin: Probable role in receptor-mediated transport of apolipoprotein J alone and in a complex with Alzheimer's disease amyloid-Aβ at the blood-brain and blood-cerebrospinal fluid barriers. Proc. Natl. Acad. Sci. USA 93:4229-4236.

Zlokovic et al. (2000) Clearance of amyloid-Aβ-peptide from brain: Transport or metabolism? Nature Med. 6:718-719.

Patents, patent applications, books, and other publications cited herein are incorporated by reference in their entirety.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transition "consisting essentially of" (i.e., allowing the inclusion of other elements to be within the scope of the claim if they do not materially affect operation of the invention) and the transition "consisting" (i.e., allowing only the elements listed in the claim other than impurities or inconse-quential activities which are ordinarily associated with the invention) instead of the "comprising" term. For example, "consisting essentially of cluster II and/or cluster IV" would allow the inclusion of other functional domains if the latter did not affect binding of Aβ while "consisting of cluster II and/or cluster IV" would prohibit the inclusion of other functional domains. Any of these three transitions can be used to claim the invention.

It should be understood that an element described in this specification should not be construed as a limitation of the claimed invention unless it is explicitly recited in the claims. For example, variants of LRP-1 are known as homologs, mutations, and polymorphisms in the known nucleotide and amino acid sequences. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A method of binding amyloid-β peptide (Aβ) in a body fluid and/or tissue of a subject, said method comprising:
   (a) providing a soluble derivative of low-density lipoprotein receptor related protein-1 (LRP-1), wherein said soluble LRP-1 derivative is comprised of cluster II, cluster IV, or both;
   (b) contacting said soluble LRP-1 derivative with at least said body fluid and/or tissue of said subject such that said Aβ is specifically bound; and
   (c) detecting said soluble LRP-1 derivative bound to Aβ.

2. The method of claim 1, wherein said soluble LRP-1 derivative binds said Aβ inside said subject's body.

3. The method of claim 1, wherein said soluble LRP-1 derivative binds said Aβ outside said subject's body.

4. The method of claim 1, wherein said soluble LRP-1 derivative bound to Aβ is removed from said subject's body.

5. The method of claim 1, wherein said soluble LRP-1 derivative bound to Aβ is inactivated such that amyloid deposits are reduced in said subject's body.

6. The method of claim 1, wherein said soluble LRP-1 derivative is comprised of cluster II.

7. The method of claim 1, wherein said soluble LRP-1 derivative is comprised of cluster IV.

8. The method of claim 1, wherein said soluble LRP-1 derivative consists essentially of cluster II, cluster IV, or both.

9. The method of claim 1, wherein said soluble LRP-1 derivative is comprised of at least one domain which mediates secretion.

10. The method of claim 1, wherein said soluble LRP-1 derivative is not comprised of a domain which mediates attachment to a lipid bilayer.

11. The method of claim 1, wherein said soluble LRP-1 derivative is reversibly attached to a solid substrate.

12. The method of claim 1, wherein said soluble LRP-1 derivative is irreversibly attached to a solid substrate.

13. The method of claim 1, wherein said soluble LRP-1 derivative is derived from human.

14. The method of claim 1, wherein said soluble LRP-1 derivative does not elicit an immune response in a human.

15. The method of claim 1, wherein said soluble LRP-1 derivative further comprises at least one heterologous domain.

16. The method of claim 15, wherein at least one detectable label is covalently attached to heterologous domain.

17. The method of claim 1, wherein at least one detectable label is covalently attached to said soluble LRP-1 derivative.

18. The method of claim 1, wherein said soluble LRP-1 derivative is comprised of both cluster II and cluster IV.

19. A method of binding amyioid-β peptide (Aβ) in a body fluid of a human subject, said method comprising:
   (a) providing a soluble fragment of low-density lipoprotein receptor related protein-1 (LRP-1) comprising cluster II, cluster IV, or both of human LRP-1;
   (b) contacting said soluble fragment of LRP-1 with at least said body fluid of said human subject such that said Aβ is specifically bound; and
   (c) detecting said soluble fragment of LRP-1 bound to Aβ.

20. The method of claim 19, wherein said soluble fragment of LRP-1 bound to Aβ is removed from said human subject's body.

21. The method of claim 19, wherein said soluble fragment of LRP-1 bound to Aβ is inactivated such that amyloid deposits are reduced in said human subject's body.

22. A method of binding amyloid-β peptide (Aβ) in a body fluid and/or tissue of a subject, said method comprising:
   (a) providing a soluble derivative of low-density lipoprotein receptor related protein-1 (LRP-1), wherein said soluble LRP-1 derivative is comprised of cluster II, cluster IV, or both;
   (b) contacting said soluble LRP-1 derivative with at least said body fluid and/or tissue of said subject such that said Aβ is specifically bound; and
   (c) removing said soluble LRP-1 derivative bound to Aβ from said subject's body.

23. The method of claim 22, wherein said soluble LRP-1 derivative binds said Aβ inside said subject's body.

24. The method of claim 22, wherein said soluble LRP-1 derivative binds said Aβ outside said subject's body.

25. The method of claim 22, wherein said soluble LRP-1 derivative bound to Aβ is inactivated such that amyloid deposits are reduced in said subject's body.

26. The method of claim 22, wherein said soluble LRP-1 derivative is comprised of cluster II.

27. The method of claim 22, wherein said soluble LRP-1 derivative is comprised of cluster IV.

28. The method of claim 22, wherein said soluble LRP-1 derivative consists essentially of cluster II, cluster IV, or both.

29. The method of claim 22, wherein said soluble LRP-1 derivative is comprised of at least one domain which mediates secretion.

30. The method of claim 22, wherein said soluble LRP-1 derivative is not comprised of a domain which mediates attachment to a lipid bilayer.

31. The method of claim 22, wherein said soluble LRP-1 derivative is reversibly attached to a solid substrate.

32. The method of claim 22, wherein said soluble LRP-1 derivative is irreversibly attached to a solid substrate.

33. The method of claim 22, wherein said soluble LRP-1 derivative is derived from human.

34. The method of claim 22, wherein said soluble LRP-1 derivative does not elicit an immune response in a human.

35. The method of claim 22, wherein said soluble LRP-1 derivative further comprises at least one heterologous domain.

36. The method of claim 35, wherein at least one detectable label is covalently attached to said heterologous domain.

37. The method of claim 22, wherein at least one detectable label is covalently attached to said soluble LRP-1 derivative.

38. The method of claim 22, wherein said soluble LRP-1 derivative is comprised of both cluster II and cluster IV.

39. A method of binding amyloid-β peptide (Aβ) in a body fluid of a human subject, said method comprising:
   (a) providing a soluble fragment of low-density lipoprotein receptor related protein-1 (LRP-1) comprising cluster II, cluster IV, or both of human LRP-1;
   (b) contacting said soluble fragment of LRP-1 with at least said body fluid of said human subject such that said Aβ is specifically bound; and
   (c) removing said soluble fragment of LRP-1 derivative bound to Aβ from said subject's body.

40. The method of claim 39, wherein said soluble fragment of LRP-1 derivative bound to Aβ is inactivated such that amyloid deposits are reduced in said human subject's body.

* * * * *